United States Patent
Hart et al.

(10) Patent No.: US 9,254,299 B2
(45) Date of Patent: Feb. 9, 2016

(54) ADMINISTRATION OF HYPOXIA ACTIVATED PRODRUGS IN COMBINATION WITH CHK1 INHIBITORS FOR TREATING CANCER

(71) Applicant: THRESHOLD PHARMACEUTICALS, INC., South San Francisco, CA (US)

(72) Inventors: Charles Hart, South San Francisco, CA (US); Fanying Meng, South San Francisco, CA (US); Jessica Sun, South San Francisco, CA (US)

(73) Assignee: Threshold Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/367,168

(22) PCT Filed: Dec. 20, 2012

(86) PCT No.: PCT/US2012/071074
§ 371 (c)(1),
(2) Date: Jun. 19, 2014

(87) PCT Pub. No.: WO2013/096687
PCT Pub. Date: Jun. 27, 2013

(65) Prior Publication Data
US 2015/0005263 A1 Jan. 1, 2015

Related U.S. Application Data

(60) Provisional application No. 61/579,605, filed on Dec. 22, 2011, provisional application No. 61/617,576, filed on Mar. 29, 2012.

(51) Int. Cl.
| | |
|---|---|
| *A61K 31/675* | (2006.01) |
| *A61K 31/4535* | (2006.01) |
| *A61K 31/5377* | (2006.01) |
| *A61K 31/5517* | (2006.01) |
| *A61K 31/34* | (2006.01) |
| *A61K 31/66* | (2006.01) |
| *A61K 45/06* | (2006.01) |
| *A61K 31/4168* | (2006.01) |

(52) U.S. Cl.
CPC ............... *A61K 31/675* (2013.01); *A61K 31/34* (2013.01); *A61K 31/4168* (2013.01); *A61K 31/4535* (2013.01); *A61K 31/5377* (2013.01); *A61K 31/5517* (2013.01); *A61K 31/66* (2013.01); *A61K 45/06* (2013.01)

(58) Field of Classification Search
USPC ........................................................ 514/94
See application file for complete search history.

(56) References Cited

U.S. PATENT DOCUMENTS

| | | |
|---|---|---|
| 5,472,956 A | 12/1995 | Borch et al. |
| 7,432,106 B2 | 10/2008 | Cox |
| 7,462,713 B2 | 12/2008 | Benedict et al. |
| 7,838,240 B2 | 11/2010 | Soyupak et al. |
| 8,946,275 B2 | 2/2015 | Curd et al. |
| 2003/0091574 A1 | 5/2003 | Gevas et al. |
| 2005/0232988 A1 | 10/2005 | Venkatesh et al. |
| 2006/0131994 A1 | 6/2006 | D'Angelico et al. |
| 2007/0117784 A1 | 5/2007 | Cleland et al. |
| 2008/0124779 A1 | 5/2008 | Oh et al. |
| 2008/0176258 A1 | 7/2008 | Pastorek et al. |
| 2009/0246271 A1 | 10/2009 | Wanebo |
| 2010/0137254 A1 | 6/2010 | Matteucci et al. |
| 2010/0183742 A1 | 7/2010 | Ammons et al. |
| 2010/0236340 A1 | 9/2010 | Lee et al. |
| 2011/0118230 A1 | 5/2011 | Chen et al. |
| 2011/0135739 A1 | 6/2011 | Carter et al. |
| 2011/0165562 A1 | 7/2011 | Pourahmadi et al. |
| 2013/0202716 A1 | 8/2013 | Curd et al. |
| 2013/0296273 A1 | 11/2013 | Curd et al. |
| 2014/0010805 A1 | 1/2014 | Hart et al. |
| 2014/0027286 A1 | 1/2014 | Ikegami et al. |
| 2014/0072624 A1 | 3/2014 | Jung et al. |
| 2014/0171389 A1 | 6/2014 | Hart et al. |
| 2015/0005262 A1 | 1/2015 | Hart et al. |
| 2015/0005264 A1 | 1/2015 | Hart et al. |

FOREIGN PATENT DOCUMENTS

| | | |
|---|---|---|
| CN | 103458880 A | 12/2013 |
| WO | WO-2007/002931 A2 | 1/2007 |
| WO | WO-2008/033041 A1 | 3/2008 |
| WO | WO-2008/083101 | 7/2008 |
| WO | WO-2009/126705 A2 | 10/2009 |
| WO | WO-2009/139915 A1 | 11/2009 |
| WO | WO-2010/048330 | 4/2010 |
| WO | WO-2010/129622 | 11/2010 |
| WO | WO-2012/006032 A2 | 1/2012 |
| WO | WO-2012/008860 | 1/2012 |
| WO | WO-2012/009288 | 1/2012 |
| WO | WO-2012/135757 | 10/2012 |
| WO | WO-2012/147426 | 11/2012 |
| WO | WO-2013/096684 | 6/2013 |
| WO | WO-2013/116385 | 8/2013 |

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Baldo et al., "mTOR pathway and mTOR inhibitors as agents for cancer therapy", Current Cancer Drug Targets 8(8): 647-665 (2008).

(Continued)

*Primary Examiner* — Kristin Vajda
(74) *Attorney, Agent, or Firm* — Foley & Lardner LLP; Antoinette F. Konski; Photon Rao

(57) ABSTRACT

Cancer can be treated by administration of TH-302 in combination with a Chk1 inhibitor.

13 Claims, 12 Drawing Sheets

(56) References Cited

OTHER PUBLICATIONS

Brenner, et al., "Phase 1/2 study of investigational hypoxia-targeted drug, TH-302, and bevacizumab (bev) in recurrent glioblastoma (GBM) following bev failure.", 2014 ASCO, May 14. Abstract doc. http://www.thresholdpharm.com/scientific_publications.
Brenner, et al.,"A Dual Phase I/II Study of TH-302 and Bevacizumab in Recurrent Glioblastoma Following Bevacizumab Failure.", 2013 WFNO/SNO, Nov. 21-24. Poster doc. http://www.thresholdpharm.com/scientific_publications.
Brenner, et al.,"Phase 1/2 Study of Investigational Hypoxia-Targeted Drug, TH-302, and Bevacizumab in Recurrent Glioblastoma Following Bevacizumab Failure.",2014 ASCO, May 7-30. http://www.thresholdpharm.com/scientific_publications.
Duan, et al., "Potent and Highly Selective Hypoxia-Activated Achiral Phosphoramidate Mustards as Anticancer Drugs", J.Med Chem (51:2412-2420) (2008).
Emmenegger, et al., "Low-dose metronomic daily cyclophosphamide and weekly Tirapazamine: A well-tolerated combination regimen with enhanced efficacy that exploits tumor hypoxia", Cancer Research, 66:(3), pp. 1664-16674, (2006).
European Search Report for EP 11807356.8 dated Oct. 28, 2013.
Extended European Search Report for EP 12764220.5 dated Oct. 10, 2014.
Friedman et al., "Bevacizumab Alone and in combination with irinotecan in recurrent glioblastoma." Journal of Clinical Oncology. 29(28):4733-4740 (2009).
International Search Report and Written Opinion dated May 23, 2013 for International Patent Application Serial No. PCT/US2013/023921.
International Search Report and Written Opinion dated Oct. 12, 2012 for International Patent Application Serial No. PCT/US201/031677.
International Search Report and Written Opinion dated Apr. 29, 2013 for International Patent Application Serial No. PCT/US2012/071070.
International Search Report and Written Opinion dated Aug. 22,2014for International Patent Application Serial No. PCT/US2014/033491.
Kumar, et al., "Preclinical Evaluation of Antitumor Efficacy of the Hypoxia-Activated Prodrug TH-302 and Sunitinib in Neuroblastoma Mouse Models.", Advances in Neuroblastoma Research (ANR) Conference, Jun. 2012. PDF doc. http://www.thresholdpharm.com/scientific_publications.
Meadows, et al. , "Phase I Study of Pazopanib in Combination with the Investigational Hypoxia-targeted Drug TH-302.", AACR-NCI-EORTC International Conference on Molecular Targets and Cancer Therapeutics, Oct. 19-23, Poster #514. Poster doc. http://www.thresholdpharm.com/scientific_publications.
Starodub, et al., "Phase 1 Study of TH-302, Investigational Hypoxia-Targeted Drug, in Combination with Sunitinib.", AACR-NCI-EORTC International Conference on Molecular Targets and Cancer Therapeutics, Oct. 19-23, Abstract No. B77. Poster doc. http://www.thresholdpharm.com/scientific_publications.
Wilson et al., "Targeting Hypoxia in Cancer Therapy," Nature Reviews Cancer 11(6): 393-410 (2011).
Zuniga, et al., "A dual phase I/II study of TH-302 and bevacizumab in resectable recurrent glioblastoma following single-agent bevacizumab failure.", European Society for Medical Oncology (ESMO) 2012 Congress, Sep. 2012. PDF doc. http://www.thresholdpharm.com/scientific_publications.
Meng, F. et al. (2011) "Molecular and Cellular Pharmacology of the Hypoxia-Activated Prodrug TH-302," Molecular Cancer Therapeutics, 11(3):740-751.
Tse, A.N. et al. (2007) "Targeting Checkpoint Kinase 1 in Cancer Therapeutics," Clinical Cancer Research, 13(7):1955-1960.
International Search Report (ISA/KR) for International Application No. PCT/US2012/071074 mailed Apr. 19, 2013, 4 pages.
Chen et al."The mTOR Inhibitor Rapamycin Suppresses DNA Double-Strand Break Repair." Radiation Research, 172(2):214-224 (2011).
Connell et al., "Genomic DNA damage and ATR-Chk1 signaling determine oncolytic adenoviral efficacy in human ovarian cancer cells.", The Journal of Clinical Investigation, 121(4):1283-1297 (2011).
Denny, W.A., "Hypoxia-activated anticancer drugs.", Expert Opinion Ther. Patents., 15(6):635-646 (2005).
Fenaux et al., "Efficacy of azacitidine compared with that of conventional care regimens in the treatment of higher-risk myelodysplastic syndromes: a randomised, open-label, phase III study," The Lancet Oncology 10:223-232 (2009).
Hart, et al., "Antiangiogenic-induced increase in tumor hypoxia in RCC and NSCLC human tumor xenografts and its selective targeting by the hypoxia-activated prodrug TH-302: A model for clinical exploration?" American Association for Cancer Research (AACR) Translational Cancer Medicine Meeting, Jul. 2010. PDF doc. http://www.thresholdpharm.com/scientific_publications.
Jung et al., "Plasma pharmacokinetics, oral bioavailability, and interspecies scaling of the hypoxically activated prodrug, TH-302, in mice, rat, dogs and monkeys." AACR Annual Meeting mOTR/Akt/PI3K Inhibitors and Vascular/Hypoxia Targeting Agents: Poster Presentations—Proffered Abstracts (2008).
National Cancer Institute. 2009. Available from:<http://web.archive.org/web/20090924062325/http://www.cancer.give/drugdisctionary/?CdrID=37944>.
RxList. "Velcade." 2010, Available from:<http://web.archive.org/web/20100124160131/http://www.rxlist.com/velcade-drug.htm>.
Supplementary European Search Report mailed Mar. 31, 2015 for European Application No. EP12860951.
Zabludoff et al., "AZD7762 A Novel Checkpoint Kinase Inhibitor Drives Checkpoint Aborgation and Potentiates Dna-Targeted Therapies", Molecular Cancer Therapeutics, 7(9):2955-2965 (2008).
Asosingh et al., "Role of the Hypoxic bone marrow microenvironment in 5T2MM murin myeloma tumor progression", The Hematology Journal, 90:810-817 (2005).
Blay, J-Y. (2010) "Updating progress in sarcoma therapy with mTOR inhibitors," Annals of Oncology:1-8.
Cavazos, D. et al. (2014) "Pharmacodynamic biomarker assessments in a phase I/II trial of the hypoxia-activated prodrug TH-302 and bevacizumab in bevacizumab-refractory recurrent glioblastoma," Neuro-Oncology 16(Suppl. 5):v60.
Chan, H-Y. et al. (2010) "Everolimus in the Treatment of Renal Cell Carcinoma and Neuroendocrine Tumors," Adv Ther. 27(8):495-511.
Cook, K.M. et al. (2010) "Angiogenesis Inhibitors—Current Strategies and Future Prospects," CA Cancer J Clin. 60(4):222-243.
Curd, J. et al. (2008) AACR Centennial Conference: Translational Cancer Medicine "Targeting tumor hypoxia with TH-302 and complementary chemotherapy," Clin Cancer Res. 14:AS.
Doloff, J.C. et al. (2009) "Increased Tumor Oxygenation and Drug Uptake During Anti-Angiogenic Weekly Low Dose Cyclophosphamide Enhances the Anti-Tumor Effect of Weekly Tirapazamine," Curr Cancer Drug Targets 9(6):777-788.
Fasolo, A. et al. (2008) "mTOR inhibitors in the treatment of cancer," Expert Opin. Investig. Drugs 17(11):1717-1734.
Hu, J. et al. (2010) "Targeting the multiple myeloma hypoxic niche with TH-302, a hypoxia-activated prodrug," Blood 116(9):1524-1527.
Kirkpatrick, J.P. et al. (2008) "Elevated CAIX Expression is Associated with an Increased Risk of Distant Failure in Early-Stage Cervical Cancer," Biomarker Insights 3:45-55.
Konopleva, M. et al. (2009) "Therapeutic targeting of microenvironmental interactions in leukemia: mechanisms and approaches," Drug Resist Updat. 12(0):103-113.
Morgan et al., "Lenalidomide (Revlimid), in combination with cyclophosphamide and dexamethasone (RCD), in an effective and tolerated regimen for myeloma patients", British Journal of Haematology, 137:268-269 (2007).
Reeder et al., "Cyclophosphamide bortezomib and dexamethasone induction for newly diagnosed multiple myeloma: high response rates in a phase II clinical trial", Leukemia, 23:1337-1341 (2009).
Supplementary European Search Report for European Application No. 13744373.5, dated Jun. 1, 2015.

(56) References Cited

OTHER PUBLICATIONS

Wind, T.C. et al. (2011) "Measuring carbonic anhydrase IX as a hypoxia biomarker: differences in concentrations in serum and plasma using a commercial enzyme-linked immunosorbent assay due to influences of metal ions," Ann Clin Biochem 48:112-120.
Non-Final Office Action in U.S. Appl. No. 13/806,088, mailed Nov. 18, 2014, 12 pages.
Final Office Action in U.S. Appl. No. 13/806,088, mailed Apr. 23, 2015, 13 pages.
Restriction Requirement in U.S. Appl. No. 13/809,135, mailed May 7, 2014, 8 pages.
Non-Final Office Action in U.S. Appl. No. 13/809,135, mailed Jul. 15, 2014, 15 pages.
Final Office Action in U.S. Appl. No. 13/809,135, mailed Feb. 20, 2015, 21 pages.
Restriction Requirement in U.S. Appl. No. 14/009,068, mailed Jul. 31, 2014, 11 pages.
Non-Final Office Action in U.S. Appl. No. 14/009,068, mailed Feb. 27, 2015, 17 pages.
Restriction Requirement in U.S. Appl. No. 14/110,819, mailed Jun. 17, 2015, 9 pages.
Non-Final Office Action in U.S. Appl. No. 14/110,819, mailed Sep. 1, 2015, 8 pages.
Restriction Requirement in U.S. Appl. No. 14/367,152, mailed Mar. 11, 2015, 9 pages.
Non-Final Office Action in U.S. Appl. No. 14/367,152, mailed Jul. 20, 2015, 11 pages.

* cited by examiner

Structure of Chk1 inhibitors

Figure 2

| Cell line | Tumor type | p53 status | Doxorubicin | | | | TH-302 (air) | | | | TH-302 (N₂) | | | |
|---|---|---|---|---|---|---|---|---|---|---|---|---|---|---|
| | | | - | +AZD7762 | +LY2603618 | +PF477736 | - | +AZD7762 | +LY2603618 | +PF477736 | - | +AZD7762 | +LY2603618 | +PF477736 |
| HeLa | Cervical | p53 -/- | 0.2 | 0.03 | 0.03 | 0.05 | >1000 | 95 | 90 | 200 | 100 | 0.5 | 0.4 | 2.1 |
| H460 | NSLCC | p53 +/+ | 0.05 | 0.05 | 0.05 | 0.05 | 25 | 25 | 22 | 19 | 0.4 | 0.2 | 0.2 | 0.2 |
| HT29 | Colon | p53 -/- | | | | | 1000 | 39 | 46 | 57 | 10 | 0.2 | 0.4 | 0.4 |
| DU145 | Prostate | p53 +/- | 0.14 | 0.05 | 0.05 | 0.05 | 210 | 80 | 110 | 340 | 2.7 | 1.1 | 0.9 | 1.9 |
| MCF10A p53⁺/⁺ | Breast | p53 +/+ | 0.05 | 0.02 | 0.04 | 0.03 | 110 | 44 | 61 | 75 | 0.8 | 0.4 | 0.5 | 0.6 |
| MCF10A p53⁻/⁻ | Breast | p53 -/- | 0.07 | 0.02 | 0.02 | 0.04 | 88 | 24 | 22 | 34 | 0.7 | 0.1 | 0.2 | 0.2 |
| SW48 p53⁺/⁺ | Colon | p53 +/+ | 0.01 | 0.02 | 0.01 | 0.02 | 39 | 16 | 35 | 39 | 0.09 | 0.04 | 0.07 | 0.2 |
| SW48 p53⁻/⁻ | Colon | p53 -/- | 0.02 | 0.02 | 0.02 | 0.04 | 110 | 19 | 22 | 27 | 1.5 | 0.2 | 0.2 | 1 |

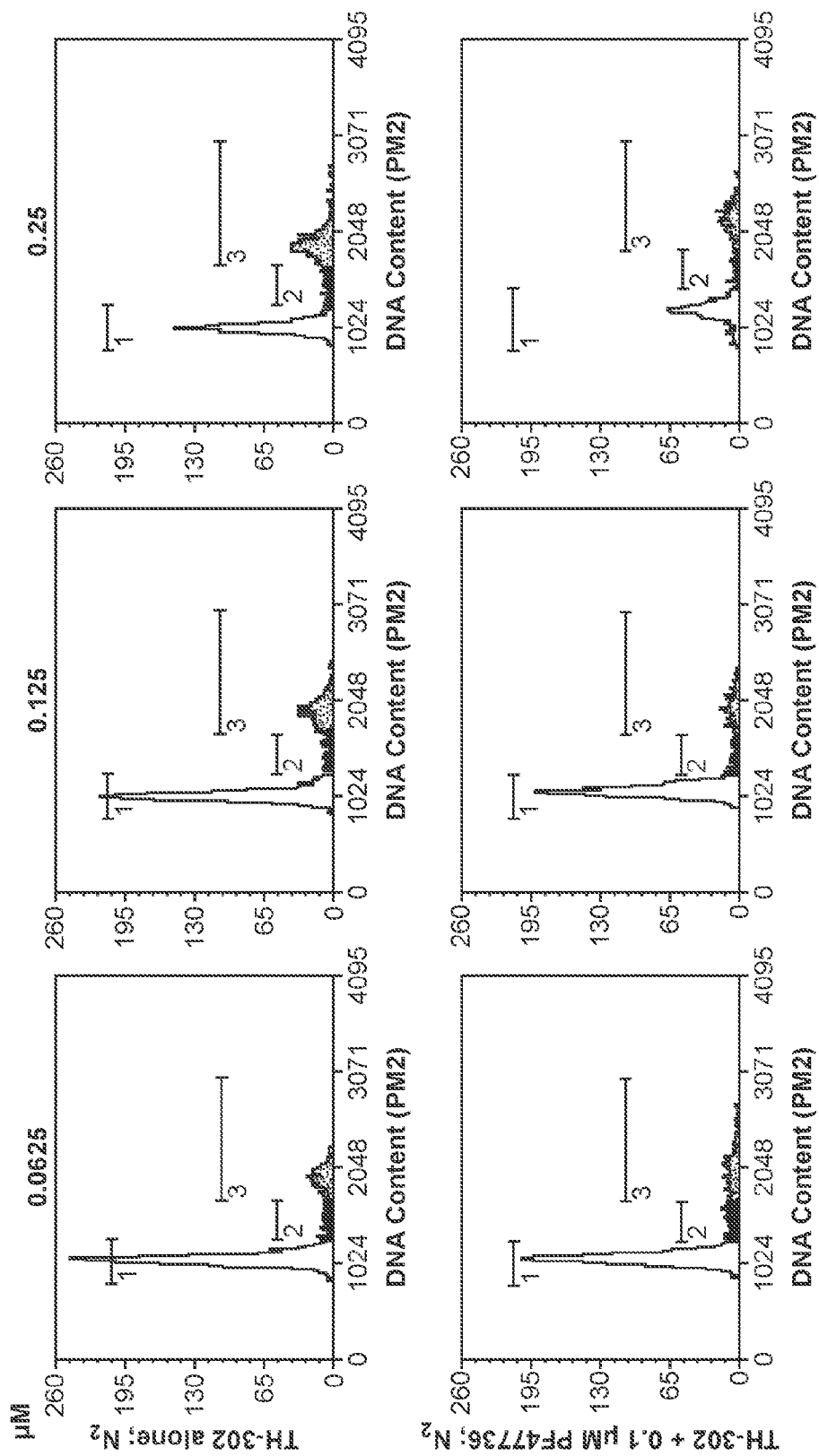
FIG. 3 (Cont. 1)

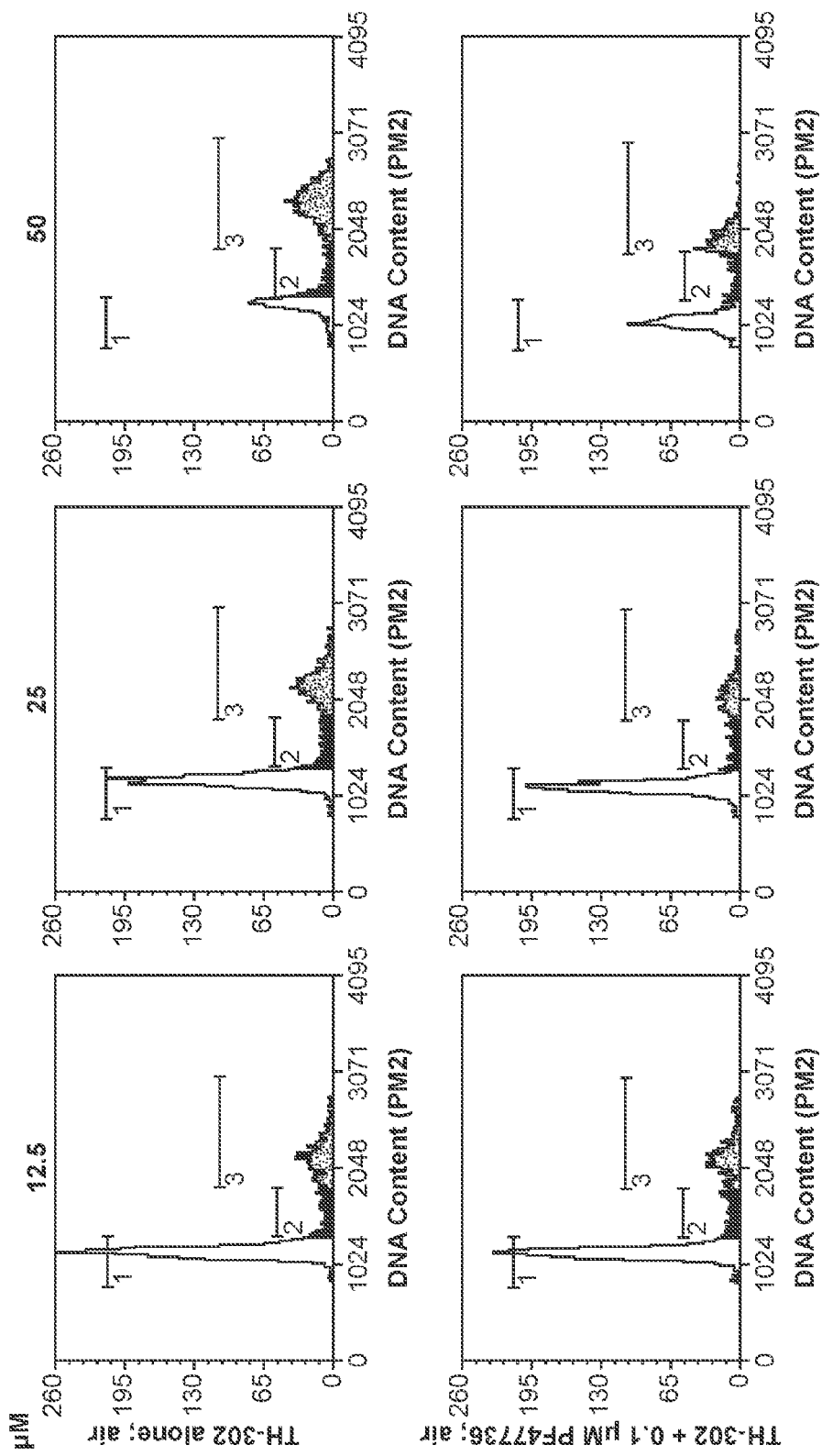
FIG. 3 (Cont. 2)

|  | TH-302 μM | TH-302 alone | | | TH-302+PF | | |
|---|---|---|---|---|---|---|---|
|  |  | %G$_0$/G$_1$ | %S | %G$_2$/M | %G$_0$/G$_1$ | %S | %G$_2$/M |
| N$_2$ | 0 | 64 | 18 | 19 |  |  |  |
|  | 0.0625 | 75 | 8 | 17 | 71 | 12 | 18 |
|  | 0.125 | 68 | 8 | 24 | 76 | 8 | 16 |
|  | 0.25 | 54 | 10 | 36 | 60 | 11 | 29 |
| Air | 12.5 | 65 | 11 | 24 | 65 | 13 | 23 |
|  | 25 | 61 | 12 | 27 | 71 | 10 | 19 |
|  | 50 | 31 | 17 | 52 | 57 | 14 | 28 |

FIG. 3 (Cont. 3)

Daily dosing

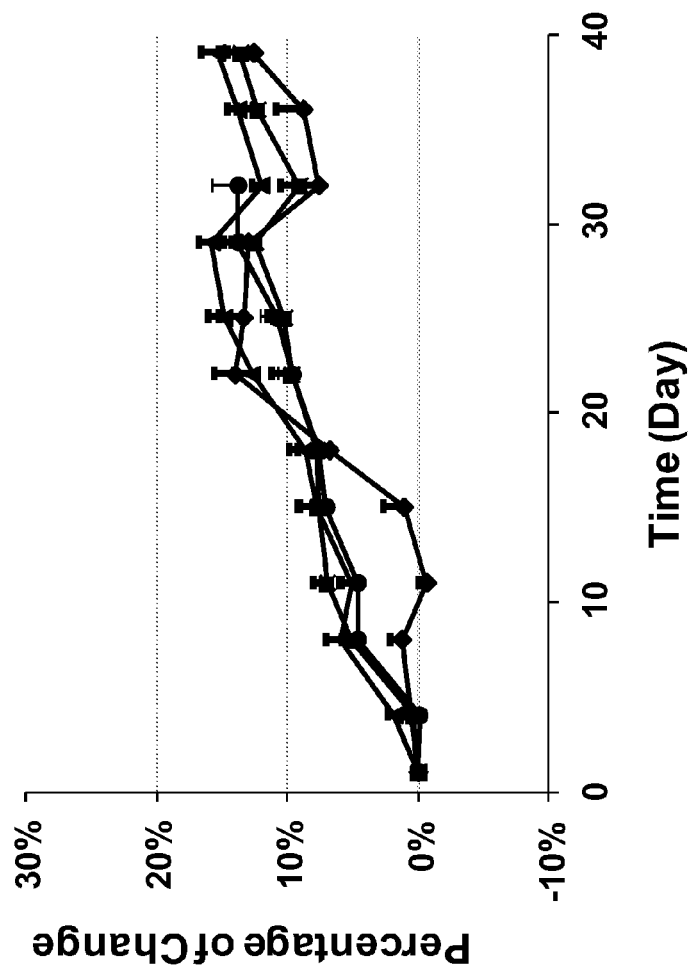
Figure 4A(II)
Daily dosing

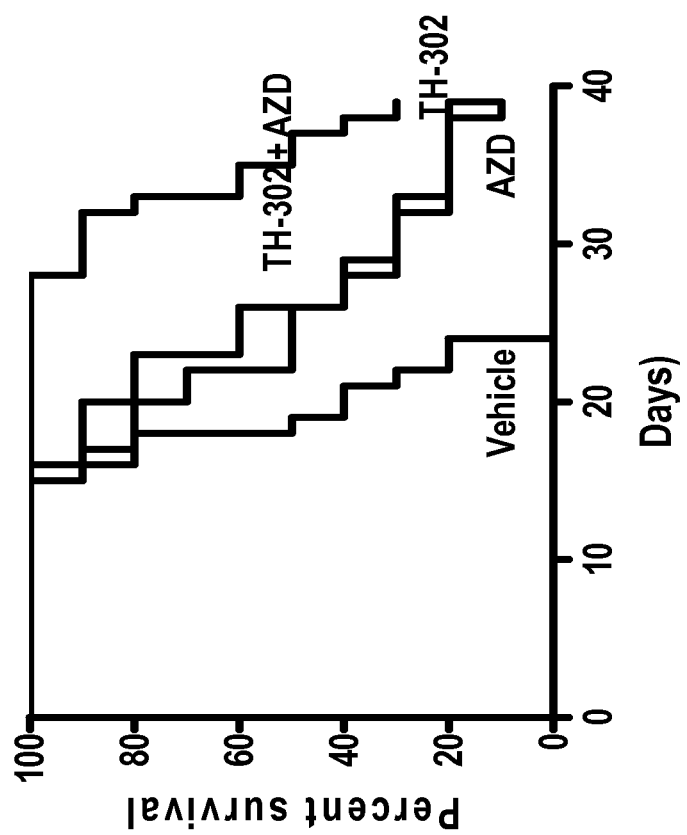
Figure 4A(III)
Daily dosing

Intermittent dosing

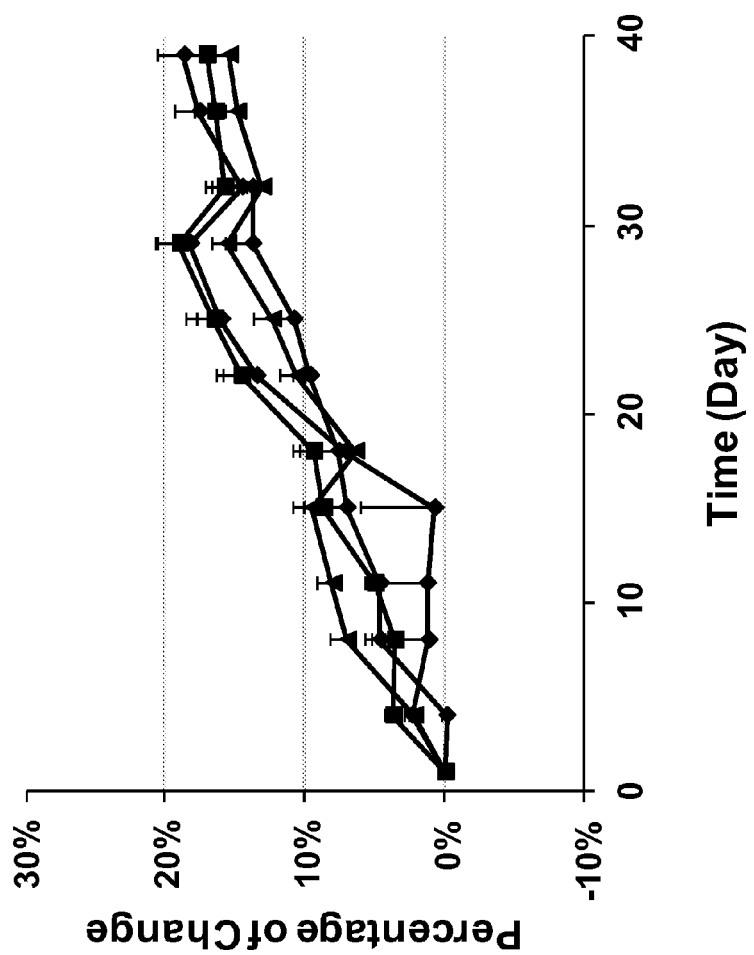
Figure 4B(II)
Intermittent dosing

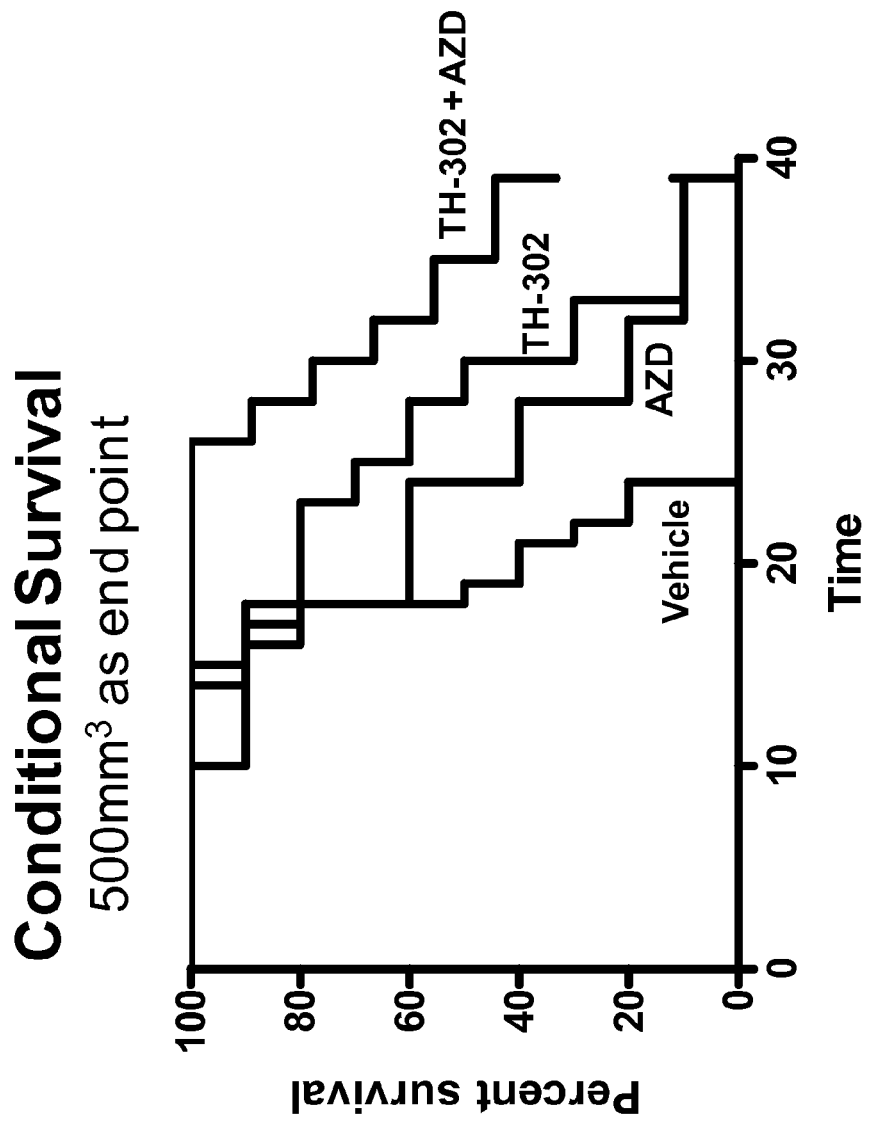
Figure 4B(III)
Intermittent dosing

ADMINISTRATION OF HYPOXIA ACTIVATED PRODRUGS IN COMBINATION WITH CHK1 INHIBITORS FOR TREATING CANCER

CROSS-REFERENCE TO RELATED APPLICATIONS

This application is a national stage application under 35 U.S.C. §371 of International Application No. PCT/US2012/071074, filed Dec. 20, 2012, which in turn claims priority under 35 U.S.C. §119(e) to U.S. Provisional Application Nos. 61/579,605 and 61/617,576, filed Dec. 22, 2011 and Mar. 29, 2012, respectively, each of which is incorporated herein in its entirety by reference.

FIELD OF THE INVENTION

The present invention provides methods for treating cancer, and pharmaceutical formulations and unit dose forms useful in those methods. The invention therefore relates to the fields of medicine and pharmacology.

BACKGROUND OF THE INVENTION

TH-302 is a hypoxia-activated prodrug in clinical development for the treatment of cancer. See PCT Publication Nos. 2007/002931; 2008/083101; 2010/048330; 2012/006032; 2012/009288; 2012/135757; 2012/142520; and U.S. provisional patent application Ser. No. 61/593,249 filed on 31 Jan. 2012, each of which is incorporated herein by reference. TH-302 releases the DNA cross-linking bromo-isophosphoramidate (sometimes referred to as bromo-isophosphoramide) mustard (Br-IPM) under hypoxic conditions. TH-302 induces $G_2/M$ arrest at low concentrations and a pan-cell cycle arrest at high concentrations.

When DNA damage occurs, a signal transduction pathway cascade is activated in response to the damage, which transmits signals to the downstream effectors that connect with the cell cycle machinery. Checkpoint kinase 1 (Chk1) is a vital link between the upstream sensors of the DNA damage checkpoints and the cell cycle effectors. See Cancer Biology & Therapy (2004) 3:3, 305-313, incorporated herein by reference. Generally, cell cycle progression is interrupted at the stage where the cell was when injured to give the cell time to repair the damage by activating DNA damage response and repair pathways. In recent years, Chk1 inhibitors have been studied for use in combination with DNA damaging anticancer agents that cause S and $G_2/M$ arrest in attempts to increase the efficacy of the underlying cancer treatment. However, no Chk1 inhibitor has been approved for cancer treatment alone or in combination with another anti cancer agent.

SUMMARY OF THE INVENTION

In a first aspect, the present invention provides a method of treating cancer, said method comprising administering to a patient in need of such treatment a therapeutically effective amount of a hypoxia activated prodrug in combination with a therapeutically effective amount of a Chk1 inhibitor.

In various embodiments, the hypoxia activated prodrug is a compound of Formula I:

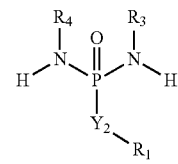

(I)

wherein $Y_2$ is O, S, $NR_6$, $NCOR_6$, or $NSO_2R_6$ wherein $R_6$ is $C_1$-$C_6$ alkyl, $C_1$-$C_6$ heteroalkyl, aryl, or heteroaryl; $R_3$ and $R_4$ are independently selected from the group consisting of 2-haloalkyl, 2-alkylsulfonyloxyalkyl, 2-heteroalkylsulfonyloxyalkyl, 2-arylsulfonyloxyalkyl, and 2-heteroalkylsulfonyloxyalkyl; $R_1$ has the formula L-$Z_3$; L is $C(Z_1)_2$; each $Z_1$ independently is hydrogen, halogen, $C_1$-$C_6$ alkyl, $C_1$-$C_6$ heteroalkyl, aryl, heteroaryl, $C_3$-$C_8$ cycloalkyl, heterocyclyl, $C_1$-$C_6$ acyl, $C_1$-$C_6$ heteroacyl, aroyl, or heteroaroyl; or L is:

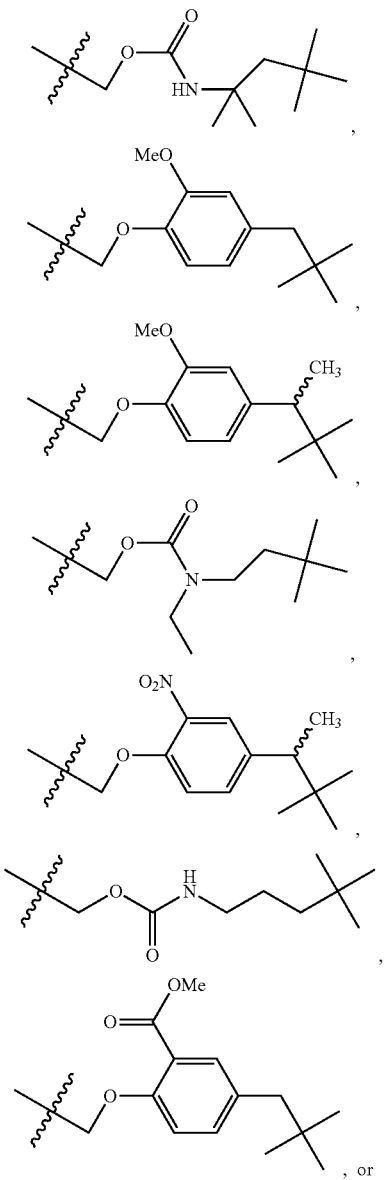

, or

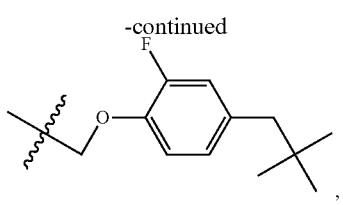

$Z_3$ is a bioreductive group having a formula selected from the group consisting of:

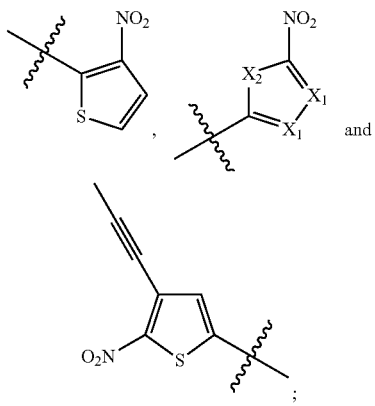

wherein each $X_1$ is independently N or $CR_8$; $X_2$ is $NR_7$, S, or O; each $R_7$ is independently $C_1$-$C_6$ alkyl, $C_1$-$C_6$ heteroalkyl, $C_3$-$C_8$ cycloalkyl, heterocyclyl, aryl or heteroaryl; and $R_9$ is independently hydrogen, halogen, cyano, $CHF_2$, $CF_3$, $CO_2H$, amino, $C_1$-$C_6$ alkyl, $C_1$-$C_6$ heteroalkyl, $C_1$-$C_6$ cycloalkyl, $C_1$-$C_6$ alkoxy, $C_1$-$C_6$ alkylamino, $C_1$-$C_6$ dialkylamino, aryl, $CON(R_7)_2$, $C_1$-$C_6$ acyl, $C_1$-$C_6$ heteroacyl, aroyl or heteroaroyl; or a pharmaceutically acceptable salt thereof. In various embodiments of the invention, the compound utilized in this invention is a compound of Formula I that is TH-281, TH-302, or TH-308 (structures provided below).

In one embodiment, the hypoxia activated drug is TH-302. In various embodiments, the TH-302 is administered at a dose and frequency described in PCT Publication Nos. 2007/002931; 2008/083101; 2010/048330; 2012/006032; 2012/009288; 2012/135757; and 2012/142520, each of which is incorporated herein by reference. In some embodiments, patients are selected for treatment and/or the efficacy of treatment is assessed in accordance with the methods described in U.S. Patent Application No. 61/593,249 filed on 31 Jan. 2012, incorporated herein by reference.

In various embodiments, the Chk1 inhibitor is an inhibitor described in Prudhomme, Recent Patents on Anti-Cancer Drug Discovery, 2006, 1, 55-68; Expert Opin. Ther. Patents (2011) 21(8): 1191-1210; and Cell Cycle (2011) 10:13, 2121-2128, each of which is incorporated herein by reference. In various embodiments, the Chk1 inhibitor is selected from the group consisting of AZD7762, LY2603618, PF-00477736, and SCH 900776. See Cancer Res. (2010) 70(12): 4972 et seq.; Clin. Cancer Res. (2010) 16(7): 2076-2084; and Shibata et al., Cancer Sci. (2011), each of which is incorporated herein by reference.

In various embodiments, the patient is identified as having a p53-deficient cancer cell prior to administration of TH-302 and the Chk1 inhibitor.

In one embodiment, the present invention provides a method of increasing antitumor effect of a compound of Formula I on a P53 deficient tumor cell, comprising coadministering to the tumor cell (or to a patient with a tumor) a Chk1 inhibitor in combination with a compound of Formula I. As used herein, "increasing the antitumor effect" of a compound of Formula I by coadministration of a Chk1 inhibitor refers to one or more of (i) increasing the number of tumor cells killed by the compound of Formula I relative to the number that would be killed in the absence of coadministration of a Chk1 inhibitor; (ii) overcoming a tumor cell's resistance to a compound of Formula I; or (iii) abrogating cell-cycle arrest, for example arrest at $G_2/M$, in a tumor cell. Coadministration, as used herein, contemplates that the two drugs coadministered exert their pharmacological effect in a tumor cell at the same time; such coadministration can be achieved by simultaneous, contemporaneous, or sequential administration of the two drugs. In one embodiment, the Chk1 inhibitor is AZD7762, PF477736, or LY603618. In another embodiment, the compound of Formula I is TH-302. In one embodiment, TH-302 is administered once daily, for five consecutive days a week. In other embodiments, TH-302 is administered no more than once a week. Within these embodiments, in some embodiments, TH-302 therapy is continued for multiple weeks.

In a second aspect, the present invention provides pharmaceutical formulations and unit dose forms suitable for use in the methods of the present invention. In one embodiment, the hypoxia activated prodrug and Chk1 inhibitor are formulated separately in distinct unit dose forms. In another embodiment, the hypoxia activated prodrug and Chk1 inhibitor are formulated together in an admixture or other combination pharmaceutical formulation and combination unit dose forms. In various embodiments, the hypoxia activated prodrug in the formulation and unit dose forms is TH-302.

BRIEF DESCRIPTION OF THE FIGURES

FIG. 2 provides a summary table of $IC_{50}$ values for various cell-based assays described in Examples 1 to 3 below.

DETAILED DESCRIPTION OF THE INVENTION

Figure 1:
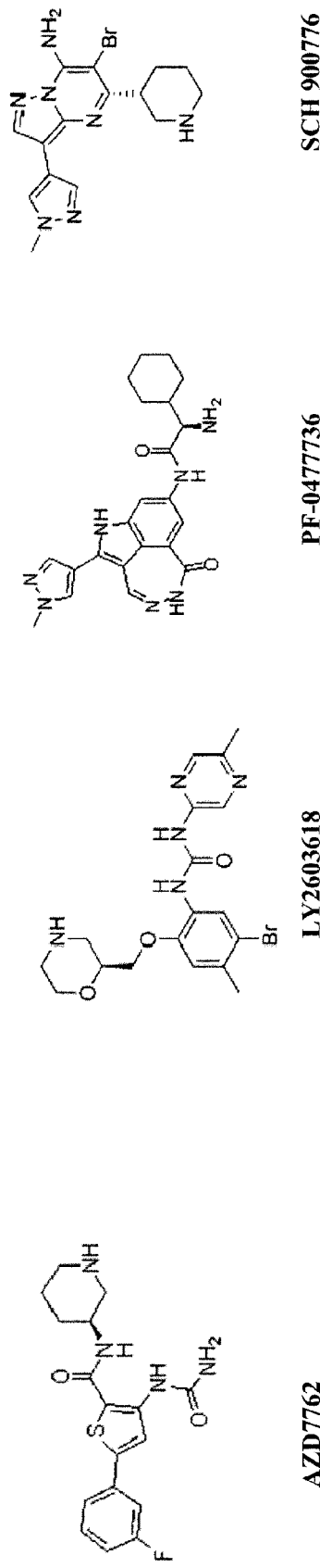
FIG. 1 shows the structures of illustrative Chk1 inhibitors.
Figure 3:
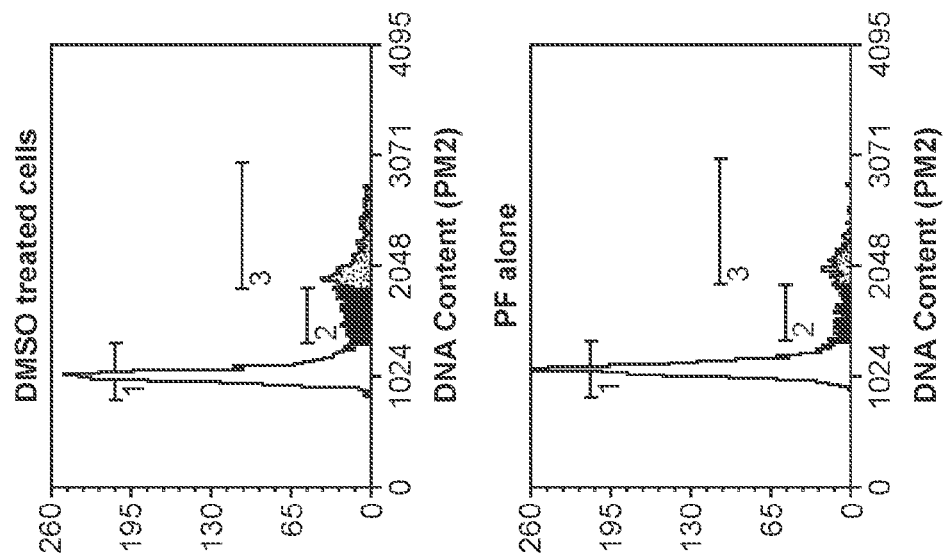
FIG. 3 shows the results of cell cycle and immunoblot analyses described in Example 4 below.

The practice of the present invention includes the use of conventional techniques of organic chemistry, molecular biology (including recombinant techniques), microbiology, cell biology, biochemistry and immunology, which are within the skill of the art.

Definitions

In this specification and in the claims that follow, reference will be made to a number of terms that have the meanings below. All numerical designations, e.g., pH, temperature, time, concentration, and weight, including ranges of each thereof, are approximations that typically may be varied (+) or (−) by increments of 0.1, 1.0, or 10.0, as appropriate. All numerical designations may be understood as preceded by the term "about". Reagents described herein are exemplary and equivalents of such may be known in the art.

The singular form "a", "an", and "the" includes plural references unless the context clearly dictates otherwise.

The term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

Certain terms related to Formula I are defined below.

"Acyl" refers to —CO— alkyl, wherein alkyl is as defined here.

"Aroyl" refers to —CO-aryl, wherein aryl is as defined here.

"Alkoxy" refers to —O-alkyl, wherein alkyl is as defined here.

"Alkenyl" refers to a linear monovalent hydrocarbon radical or a branched monovalent hydrocarbon radical having the number of carbon atoms indicated in the prefix and containing at least one double bond, but no more than three double bonds. For example, ($C_2$-$C_6$)alkenyl includes, ethenyl, propenyl, 1,3-butadienyl and the like. Alkenyl can be optionally substituted with substituents, including for example, deuterium ("D"), hydroxyl, amino, mono or di($C_1$-$C_6$)alkyl amino, halo, $C_2$-$C_6$ alkenyl ether, cyano, nitro, ethynyl, $C_1$-$C_6$ alkoxy, $C_1$-$C_6$ alkylthio, —COOH, —CONH$_2$, mono- or di($C_1$-$C_6$)alkylcarboxamido, —SO$_2$NH$_2$, —OSO$_2$—($C_1$-$C_6$) alkyl, mono or di($C_1$-$C_6$)alkylsulfonamido, aryl, heteroaryl, alkyl or heteroalkylsulfonyloxy, and aryl or heteroarylsulfonyloxy.

"Alkyl" refers to a linear saturated monovalent hydrocarbon radical or a branched saturated monovalent hydrocarbon radical having the number of carbon atoms indicated in the prefix. ($C_1$-$C_6$)alkyl can be optionally substituted with substituents, including for example, deuterium ("D"), hydroxyl, amino, mono or di($C_1$-$C_6$)alkyl amino, halo, $C_2$-$C_6$ alkenyl ether, cyano, nitro, ethenyl, ethynyl, $C_1$-$C_6$ alkoxy, $C_1$-$C_6$ alkylthio, —COOH, —CONH$_2$, mono- or di($C_1$-$C_6$)alkylcarboxamido, —SO$_2$NH$_2$, —OSO$_2$—($C_1$-$C_6$)alkyl, mono or di($C_1$-$C_6$)alkylsulfonamido, aryl, heteroaryl, alkylsulfonyloxy, heteroalkylsulfonyloxy, arylsulfonyloxy or heteroarylsulfonyloxy.

The prefixes ($C_1$-$C_{qq}$), $C_{1-qq}$, and $C_1$-$C_{qq}$, wherein qq is an integer from 2-20, have the same meaning. For example, ($C_1$-$C_6$)alkyl, $C_{1-6}$ alkyl, or $C_1$-$C_6$ alkyl includes methyl, ethyl, n-propyl, 2-propyl, n-butyl, 2-butyl, tert-butyl, pentyl, and the like. For each of the definitions herein (e.g., alkyl, alkenyl, alkoxy, etc.), when a prefix is not included to indicate the number of main chain carbon atoms in an alkyl portion, the radical or portion thereof will have six or fewer main chain carbon atoms.

"Alkylamino" or mono-alkylamino refers to —NH-alkyl, wherein alkyl is as defined here.

"Alkynyl" refers to a linear monovalent hydrocarbon radical or a branched monovalent hydrocarbon radical having the number of carbon atoms indicated in the prefix and containing at least one triple bond, but no more than two triple bonds. For example, ($C_2$-$C_6$)alkynyl includes, ethynyl, propynyl, and the like. Alkynyl can be optionally substituted with substituents, including for example, deuterium ("D"), hydroxyl, amino, mono or di($C_1$-$C_6$)alkyl amino, halo, $C_2$-$C_6$ alkenyl ether, cyano, nitro, ethenyl, $C_1$-$C_6$ alkoxy, $C_1$-$C_6$ alkylthio, —COOH, —CONH$_2$, mono- or di($C_1$-$C_6$)alkylcarboxamido, —SO$_2$NH$_2$, —OSO$_2$—($C_1$-$C_6$)alkyl, mono or di($C_1$-$C_6$)alkylsulfonamido, aryl, heteroaryl, alkyl or heteroalkylsulfonyloxy, and aryl or heteroarylsulfonyloxy.

"Aryl" refers to a monovalent monocyclic or bicyclic aromatic hydrocarbon radical of 6 to 10 ring atoms which is substituted independently with one to eight substituents, e.g. one, two, three, four of five substituents selected from deuterium ("D"), alkyl, cycloalkyl, cycloalkylalkyl, halo, nitro, cyano, hydroxyl, alkoxy, amino, acylamino, mono-alkylamino, di-alkylamino, haloalkyl, haloalkoxy, heteroalkyl, COR (where R is hydrogen, alkyl, cycloalkyl, cycloalkylalkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$_n$—CONR$^x$R$^y$ (where n is an integer from 0 to 5, R' and R" are independently hydrogen or alkyl, and R$^x$ and R$^y$ are independently selected from hydrogen, alkyl, cycloalkyl, cycloalkylalkyl, phenyl or phenylalkyl). In one embodiment, R$^x$ and R$^y$ together is cycloalkyl or heterocyclyl. More specifically the term aryl includes, but is not limited to, phenyl, biphenyl, 1-naphthyl, and 2-naphthyl, and the substituted forms thereof.

"Cycloalkyl" refers to a monovalent cyclic hydrocarbon radical of three to seven ring carbons. The cycloalkyl group can have one or more double bonds and can also be optionally substituted independently with one, two, three or four substituents selected from alkyl, optionally substituted phenyl, or —C(O)R$^z$ (where R$^z$ is hydrogen, alkyl, haloalkyl, amino, mono-alkylamino, di-alkylamino, hydroxyl, alkoxy, or optionally substituted phenyl). More specifically, the term cycloalkyl includes, for example, cyclopropyl, cyclohexyl, cyclohexenyl, phenylcyclohexyl, 4-carboxycyclohexyl, 2-carboxamidocyclohexenyl, 2-dimethylaminocarbonyl-cyclohexyl, and the like.

"Dialkylamino" or di-alkylamino refers to —N(alkyl)$_2$, wherein alkyl is as defined here.

"Heteroalkyl" refers to an alkyl radical as defined herein with one, two or three substituents independently selected from cyano, —OR$^w$, —NR$^x$R$^y$, and —S(O)$_p$R$^z$ (where p is an integer from 0 to 2), with the understanding that the point of attachment of the heteroalkyl radical is through a carbon atom of the heteroalkyl radical. R$^w$ is hydrogen, alkyl, cycloalkyl, cycloalkyl-alkyl, aryl, aralkyl, alkoxycarbonyl, aryloxycarbonyl, carboxamido, or mono- or di-alkylcarbamoyl. R$^x$ is hydrogen, alkyl, cycloalkyl, cycloalkyl-alkyl, aryl or araalkyl. R$^y$ is hydrogen, alkyl, cycloalkyl, cycloalkyl-alkyl, aryl, araalkyl, alkoxycarbonyl, aryloxycarbonyl, carboxamido, mono- or di-alkylcarbamoyl or alkylsulfonyl. R$^z$ is hydrogen (provided that p is 0), alkyl, cycloalkyl, cycloalkyl-alkyl, aryl, araalkyl, amino, mono-alkylamino, di-alkylamino, or hydroxyalkyl. Representative examples include, for example, 2-hydroxyethyl, 2,3-dihydroxypropyl, 2-methoxyethyl, benzyloxymethyl, 2-cyanoethyl, and 2-methylsulfonyl-ethyl. For each of the above, R$^w$, R$^x$, R$^y$, and R$^z$ can be further substituted by amino, halo, fluoro, alkylamino, di-alkylamino, OH or alkoxy. Additionally, the prefix indicating the number of carbon atoms (e.g., $C_1$-$C_{10}$) refers to the total number of carbon atoms in the portion of the heteroalkyl group exclusive of the cyano, —OR$^w$, —NR$^x$R$^y$, or —S(O)$_p$R$^z$ portions. In one embodiment, R$^x$ and R$^y$ together is cycloalkyl or heterocyclyl.

"Heteroaryl" refers to a monovalent monocyclic, bicyclic or tricyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring is optionally substituted independently with one to eight substituents, preferably one, two, three or four substituents, selected from alkyl, cycloalkyl, cycloalkyl-alkyl, halo, nitro, cyano, hydroxyl, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkyl-alkyl, phenyl or phenylalkyl), or —(CR'R")$_n$—CONR$^x$R$^y$ (where n is an integer from 0 to 5, R' and R" are independently hydrogen or alkyl, and R$^x$ and R$^y$ are, independently of each other, hydrogen, alkyl, cycloalkyl, cycloalkyl-alkyl, phenyl or phenylalkyl). In one embodiment, R$^x$ and R$^y$ together is cycloalkyl or heterocyclyl. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyridazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl, benzothienyl, indazolyl, pyrrolopyrymidinyl, indolizinyl, pyrazolopyridinyl, triazolopyridinyl, pyrazolopyrimidinyl, triazolopyrimidinyl, pyrrolotriazinyl, pyrazolotriazinyl, triazolotriazinyl, pyrazolotetrazinyl, hexaaza-indenly, and heptaaza-indenyl and the derivatives thereof. Unless indicated otherwise, the arrangement of the hetero atoms within the ring can be any arrangement allowed by the bonding characteristics of the constituent ring atoms.

"Heterocyclyl" or "cycloheteroalkyl" refers to a saturated or unsaturated non-aromatic cyclic radical of 3 to 8 ring atoms in which one to four ring atoms are heteroatoms selected from O, NR (where R is hydrogen, alkyl, cycloalkyl, cycloalkylalkyl, phenyl or phenylalkyl), P(=O)OR$^w$, or S(O)$_p$ (where p is an integer from 0 to 2), the remaining ring atoms being C, wherein one or two C atoms can optionally be replaced by a carbonyl group. The heterocyclyl ring can be optionally substituted independently with one, two, three or four substituents selected from alkyl, aryl, arylalkyl, heteroaryl, heteroarylalkyl, cycloalkyl, cycloalkylalkyl, halo, nitro, cyano, hydroxyl, alkoxy, amino, mono-alkylamino, di-alkylamino, haloalkyl, haloalkoxy, —COR (where R is hydrogen, alkyl, cycloalkyl, cycloalkylalkyl, phenyl or phenylalkyl), —(CR'R")$_n$—COOR (n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^x$R$^y$ (where n is an integer from 0 to 5, R' and R" are independently hydrogen or alkyl, R$^x$ and R$^y$ are, independently of each other, hydrogen, alkyl, cycloalkyl, cycloalkylalkyl, phenyl or phenylalkyl). More specifically the term heterocyclyl includes, but is not limited to, tetrahydropyranyl, N-methylpiperidin-3-yl, N-methylpyrrolidin-3-yl, 2-pyrrolidon-1-yl, pyrrolidinyl, piperidinyl, morpholinyl, tetrahydrofuranyl, tetrahydrothiofuranyl, 1,1-dioxo-hexahydro-1Δ$^6$-thiopyran-4-yl, tetrahydroimidazo[4,5-c]pyridinyl, imidazolinyl, piperazinyl, and piperidin-2-yl and the derivatives thereof. The prefix indicating the number of carbon atoms (e.g., C$_3$-C$_{10}$) refers to the total number of carbon atoms in the portion of the cycloheteroalkyl or heterocyclyl group exclusive of the number of heteroatoms.

"Heteroacyl" refers to —CO-heteroalkyl, wherein heteroalkyl is as defined here.

"Heteroaroyl" refers to —CO-heteroayl, wherein heteroaryl is as defined here.

"R$_{sul}$ sulfonyloxy" refers to R$_{sul}$—S(=O)$_2$—O— and includes alkylsulfonyloxy, heteroakylsulfonyloxy, cycloalkylsulfonyloxy, heterocyclylsulfonyloxy, arylsulfonyloxy and heteroarylsulfonyloxy wherein R$_{sul}$ is alkyl, heteroakyl, cycloalkyl, heterocyclyl, aryl and heteroaryl respectively, and wherein alkyl, heteroakyl, cycloalkyl, heterocyclyl, aryl and heteroaryl are as defined here. Examples of alkylsulfonyloxy include Me-S(=O)$_2$—O—, Et-S(=O)$_2$—O—, CF$_3$—S(=O)$_2$—O— and the like, and examples of arylsulfonyloxy include:

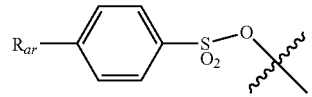

wherein R$_{ar}$ is H, methyl, or bromo.

"Substituents" refer to, along with substituents particularly described in the definition of each of the groups above, those selected from: deuterieum, -halogen, —OR', —NR'R", —SR', —SiR'R"R"', —OC(O)R', —C(O)R', —CO$_2$R', —CONR'R", —OC(O)NR'R", —NR"C(O)R', —NR'—C(O)NR'R"', —NR"C(O)$_2$R', —NH—C(NH$_2$)=NH, —NR'C(NH)=NH, —NH—C(NH$_2$)=NR', —S(O)R', —S(O)$_2$R', —S(O)$_2$NR'R", —NR'S(O)$_2$R", —CN, —NO$_2$, —R', —N$_3$, perfluoro(C$_1$-C$_4$)alkoxy, and perfluoro(C$_1$-C$_4$)alkyl, in a number ranging from zero to the total number of open valences on the radical; and where R', R" and R"' are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl, aryl substituted with 1-3 halogens, unsubstituted C$_{1-8}$ alkyl, C$_{1-8}$alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other suitable substituents include each of the above aryl substituents attached to a ring atom by an alkylene tether of from 1-4 carbon atoms. Two of the substituents on adjacent atoms of the aryl or heteroaryl ring may optionally be replaced with a substituent of the formula -T$^2$-C(O)—(CH$_2$)$_q$-U$^3$-, wherein T$^2$ and U$^3$ are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B-, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X$^5$—(CH$_2$)$_t$—, wherein s and t are independently integers of from 0 to 3, and X$^5$ is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

Certain compounds utilized in the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example, and without limitation, tritium ($^3$H), iodine-125 ($^{125}$I), or carbon-14 ($^{14}$C). All isotopic variations of the compounds of the present invention, whether radioactive or not, are intended to be encompassed within the scope of the present invention.

Other terms related to this invention are defined below.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Cancer" refers to malignant solid tumors of potentially unlimited growth, as well as various blood cancers that may originate from cancer stem cells in the bone marrow, which can expand locally by invasion and systemically by metastasis. Examples of cancers include, but are not limited to, cancer of the adrenal gland, bone, brain, breast, bronchi, colon and/or rectum, gallbladder, gastrointestinal tract, head and neck, kidneys, larynx, liver, lung, neural tissue, pancreas, prostate, parathyroid, skin, stomach, and thyroid. Other examples of cancers include, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myelodisplastic syndrome, myeloma, mycosis fungoides, neuroblastoma, osteosarcoma, osteogenic and other sarcoma, ovarian tumor, pheochromocytoma, polycythermia vera, primary brain tumor, small-cell lung tumor, squamous cell carcinoma of both ulcerating and papillary type, seminoma, soft tissue sarcoma, retinoblastoma, rhabdomyosarcoma, renal cell tumor or renal cell carcinoma, veticulum cell sarcoma, and Wilm's tumor. Examples of cancers also include astrocytoma, a gastrointestinal stromal tumor (GIST), a glioma or glioblastoma, renal cell carcinoma (RCC), hepatocellular carcinoma (HCC), and a pancreatic neuroendocrine cancer.

"Combination therapy" or "combination treatment" refers to the use of two or more drugs in therapy, i.e., use of a hypoxia activated prodrug as described herein together with one or more Chk1 inhibitors, and optionally one or more other anti cancer agent(s), to treat cancer. Administration in "combination" refers to the administration of two or more agents (e.g., a hypoxia activated prodrug and a Chk1 inhibitor, and optionally one or more anti cancer agents, for treating cancer) in any manner in which the pharmacological effects of both are manifest in the patient at the same time. Thus, administration in combination does not require that a single pharmaceutical composition, the same dosage form, or the same route of administration be used for administration of both agents or that the two agents be administered at precisely the same time. For example, and without limitation, it is contemplated that a Chk1 inhibitor can be administered with a hypoxia activated prodrug in accordance with the present invention as a combination therapy.

"Hyperproliferative disease" refers to a disease characterized by cellular hyperproliferation (e.g., an abnormally increased rate or amount of cellular proliferation). Cancer is a hyperproliferative disease. Examples of hyperproliferative diseases other than cancer include, but are not limited to, allergic angiitis and granulomatosis (Churg-Strauss disease), asbestosis, asthma, atrophic gastritis, benign prostatic hyperplasia, bullous pemphigoid, coeliac disease, chronic bronchitis and chronic obstructive airway disease, chronic sinusitis, Crohn's disease, demyelinating neuropathies, dermatomyositis, eczema including atopic dermatitis, eustachean tube diseases, giant cell arteritis, graft rejection, hypersensitivity pneumonitis, hypersensitivity vasculitis (Henoch-Schonlein purpura), irritant dermatitis, inflammatory hemolytic anemia, inflammatory neutropenia, inflammatory bowel disease, Kawasaki's disease, multiple sclerosis, myocarditis, myositis, nasal polyps, nasolacrimal duct diseases, neoplastic vasculitis, pancreatitis, pemphigus vulgaris, primary glomerulonephritis, psoriasis, periodontal disease, polycystic kidney disease, polyarteritis nodosa, polyangitis overlap syndrome, primary sclerosing cholangitis, rheumatoid arthritis, serum sickness, surgical adhesions, stenosis or restenosis, scleritis, scleroderma, strictures of bile ducts, strictures (of duodenum, small bowel, and colon), silicosis and other forms of pneumoconiosis, type I diabetes, ulcerative colitis, ulcerative proctitis, vasculitis associated with connective tissue disorders, vasculitis associated with congenital deficiencies of the complement system, vasculitis of the central nervous system, and Wegener's granulomatosis.

"Hypoxia activated prodrug" refers to a drug that is less active or inactive under normoxia than under hypoxia or anoxia. Hypoxia activated prodrugs include drugs that are activated by a variety of reducing agents, including without limitation single electron transferring enzymes (such as cytochrome P450 reductases) and two electron transferring (or hydride transferring) enzymes (see U.S. Pat. App. Pub. Nos. 2005/0256191, 2007/0032455, and 2009/0136521, and PCT Pub. Nos. 2000/064864, 2004/087075, and 2007/002931, each of which is incorporated herein by reference). The hypoxia activated prodrugs useful in the methods of the present invention are compounds of Formula I, including but not limited to compounds where $Z_3$, as defined by that formula, is a 2-nitroimidazole moiety. Examples of particular hypoxia activated prodrugs useful in the methods of the invention include without limitation TH-281, TH-302, and TH-308. Methods of synthesizing, formulating, and using TH-302 and other compounds of Formula I are described in in the various patent publications and applications referenced in the "Background of the Invention", above, which are incorporated herein by reference.

"Chk1" or cell cycle checkpoint kinase 1 refers to serine/threonine-protein kinase that in humans is encoded by the CHEK1 gene. Chk1 is a kinase that phosphorylates Cdc25, an important phosphatase in cell cycle control, particularly for entry into mitosis. Cdc25 is a dual phosphatase responsible for dephosphorylation and activation of Cdc2 kinase, which is a cell cycle kinase responsible for the regulation of G2 progression and G2-M transition, in G2. Cdc25, when phosphorylated by Chk1, becomes bound by an adaptor protein in the cytoplasm. Inhibition of Cdc25 blocks cell cycle progression and, consequently, prevents a cell from entering mitosis.

"Chk1 inhibitor" refers to a compound that inhibits Chk1. Without being bound by theory, Chk1 inhibitors can potentiate the anti cancer efficacy of various DNA damaging agents by overriding the last checkpoint defense against DNA damaging agent-induced lethal damage. By binding to and inhibiting Chk1, Chk1 inhibitors can cause tumor cells, which might otherwise bypass Chk1-dependent cell cycle arrest in the S and G2/M phases, to undergo DNA repair prior to entry into mitosis. Tumor cells can thus be sensitized to the DNA-damaging effects of alkylating chemotherapeutic agents. Furthermore, the Chk1 inhibitors' action may lead to an accumulation of damaged DNA and promote genomic instability and apoptosis of the cancer cell. Examples of Chk1 inhibitors include, without limitation AZD7762, CHIR-124, LY2603618, LY2606368, PF-477736, and SCH 900776.

Other examples of Chk1 inhibitor are provided in Prudhomme, Recent Patents on Anti-Cancer Drug Discovery, 2006, 1, 55-68; Expert Opin. Ther. Patents (2011) 21(8): 1191-1210; and Cell Cycle (2011) 10:13, 2121-2128, each of which is incorporated herein by reference in its entirety. The structures of illustrative Chk1 inhibitors are shown in FIG. 1.

The term "p53 deficient" refers to a cancer cell having mutated p53 or substantially no p53. The p53 molecule (also known as protein 53 or tumor protein 53) is a tumor suppressor protein that in humans is encoded by the TP53 gene.

"Patient" or "subject" refers to mammals, particularly humans, and so includes animals of veterinary and research interest, such as simians, cattle, horses, dogs, cats, and rodents with cancer or another hyperproliferative disease.

"Pharmaceutically acceptable salt" refers to pharmaceutically acceptable salts derived from a variety of organic and inorganic counter ions well known in the art that include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in Stahl and Wermuth (Eds.), Handbook of Pharmaceutical Salts Properties, Selection, and Use; 2002.

QnD or qnd refers to drug administration once every n days. For example, QD (or qd) refers to once every day or once daily dosing, Q2D (or q2d) refers to a dosing once every two days, Q7D refers to a dosing once every 7 days or once a week, Q5D refers to dosing once every 5 days.

"Reduction" of a symptom or symptoms (and grammatical equivalents of this phrase) refers to decreasing the severity or frequency of the symptom(s), or elimination of the symptom(s).

"Relapsed or refractory" refers to a type of cancer that is resistant to treatment with an agent, such a Chk1 inhibitor or a hypoxia activated prodrug, or responds to treatment with an agent but recurs with or without being resistant to that agent.

TH-281 refers to the compound of formula:

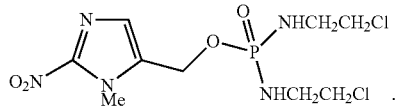

TH-302 refers to the compound of formula:

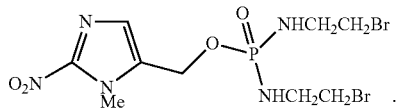

TH-308 refers to the compound of formula:

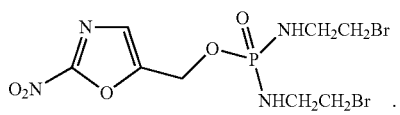

"Therapeutically effective amount" of a drug or an agent refers to an amount of the drug or the agent that, when administered to a patient with cancer or another hyperproliferative disease, will have the intended therapeutic effect, e.g., alleviation, amelioration, palliation or elimination of one or more manifestations of cancer or another hyperproliferative disease in the patient. A therapeutic effect does not necessarily occur by administration of one dose, and may occur only after administration of a series of doses. Thus, a therapeutically effective amount may be administered in one or more administrations.

"Treating" or "treatment of" a condition or patient refers to taking steps to obtain beneficial or desired results, including clinical results. For purposes of this invention, beneficial or desired clinical results include, but are not limited to, alleviation or amelioration of one or more symptoms of cancer or another hyperproliferative disease including conditional survival and reduction of tumor load or volume; diminishment of extent of disease; delay or slowing of disease progression; amelioration, palliation, or stabilization of the disease state; or other beneficial results.

The present invention arises in part from the discovery that the pharmacological inhibition of Chk1 kinase activity can potentiate the efficacy of TH-302 and other drugs of Formula I, when administered in accordance with the methods of the invention. As the examples below demonstrate, three different Chk1 inhibitors (PF477736, AZD7762 and LY2603618) in combination with TH-302 show increased anti cancer efficacy in HeLa cervical, and HT-29 colon, and not in H460 non-small cell lung cell lines. As demonstrated in a 3-day in vitro proliferation assay with AlamarBlue as a read-out, TH-302 activity is greatly enhanced (15 to 50 fold) by the presence of any one of these three Chk1 inhibitors in the two p53-deficient cell lines (Hela and HT29) tested. In contrast, TH-302 activity is not affected by the presence of the Chk1 inhibitors in the p53 wild-type line (H460). These results were confirmed in a clonogenic survival-based assay. In addition, as described in the examples below, an HT29 xenograft animal model was used to demonstrate that AZD7762 enhances the antitumor activity of TH-302.

Normal cells typically have two mechanisms for repairing DNA damage, one mediated by the p53 pathway and the other mediated by the Chk1 pathway. Each of these pathways arrests the cell in its mitotic cycle so that the DNA damage can be repaired prior to cell division, during which the DNA damage, if left unrepaired, could trigger apoptotic pathways, leading to cell death. In many tumor cells, the p53 pathway is inactivated by mutation, making the tumor especially sensitive to the combination therapies of the invention. For example, more than half of all bladder, colon, head/neck, lung, and ovarian cancers have been reported to have p53 mutations (be p53-deficient). Accordingly, in some embodiments, cancer patients to be treated in accordance with the methods of the invention will not be pre-screened to determine p53 status.

However, in other embodiments of the invention, patients are screened to determine if their cancer is p53-deficient prior to administration of a combination therapy of the invention. Patients most likely to respond favorably to treatment with the combination therapies of the invention are p53-deficient. Whether p53 is present or not, whether p53 is mutated, or whether p53 is over expressed in a cancer cell is readily determined via methods well known to a skilled artisan, such as immunohistochemistry and reverse transcriptase polymerase chain reaction (RTPCR). For example, suitable methods for assessing p53 status are described in Chiaretti et al., 2011, Genes, Chrom. & Cancer 50: 263-274; and Berglind et al., 2008, Cancer Biol. & Ther. 7: 5, 699-708, each of which is incorporated herein by reference. Moreover, commercially available test kits, such as the AmpliChip p53 Test (Roche)

can be used to assess p53 status of cancer cells from a patient. In some embodiments, patients screened to be p53-deficient are administered the compound of Formula I, e.g., TH-302 in combination with a Chk1 inhibitor, in accordance with the present invention.

While the invention is not to be limited by any theory of mechanism of action, TH-302 is believed to induce cell-cycle arrest at the $G_2$/M phase mediated by activation of Chk1 and prevention of the activation of downstream Cdc2 kinase activity. The results in the examples below show that Chk1 inhibitors can abrogate TH-302-induced $G_2$ checkpoint arrest in Hela and other p53-deficient cells. Chk1 affects Cdc2 phosphorylation, and, as reported in the examples below, Cdc2 phosphorylation was evaluated in response to the Chk1 inhibitor alone, TH-302 alone, and the combination of a Chk1 inhibitor and TH-302. The results demonstrated that TH-302 alone, but not a Chk1 inhibitor alone, increases Cdc2-Y15 phosphorylation due to the induced $G_2$/M arrest. In the combination study, the addition of the Chk1 inhibitor blocks the TH-302-induced increase of Cdc2-Y15 phosphorylation. Taken together, the results support that efficacious treatment of cancer can be achieved by administering one or more Chk1 inhibitors in combination with tumor-hypoxia targeting hypoxia activated prodrugs of Formula I, such as, TH-302, optionally in combination with other anti-cancer agents.

In various embodiments of the invention TH-302, or another compound of Formula I, is administered in combination with a Chk1 inhibitor to treat cancer. Administration of a number of Chk1 inhibitors, for example and without limitation, AZD7762, LY2603618, SCH 900776, PF-00477736 (se below and FIG. 1) have been demonstrated for once-a-week administration. In various embodiments of the combination therapies of the invention, a Chk1 inhibitor is administered, at a dosing amount reported (for example, and without limitation, see below), no more frequently than once per week, and in many of these embodiments, a patient receives multiple doses, over a period of many weeks to several months or longer, of the Chk1 inhibitor. As described more fully below, TH-302 and the other compounds of Formula I can be conveniently administered at a frequency of no more than once per week, and in various embodiments of the invention, TH-302 or another compound of Formula I is administered in combination with the Chk1 inhibitor administered as described above, and both compounds are administered no more frequently than once per week. In various of these embodiments, TH-302 or another compound of Formula I is administered in cycles of four weeks, in which TH-302 is administered once per week for three consecutive weeks and is not administered in the fourth week. In various of these embodiments, TH-302 or another compound of Formula I is administered in cycles of three weeks, where TH-302 is administered once per week for two consecutive weeks and is not administered in the third week or where TH-302 is administered only in the first week of the three week cycle. In any of these embodiments, where the compound is TH-302, the dose can be as described below, i.e., 240-670 mg/m². When a compound of Formula I and a Chk1 inhibitor are coadministered on the same day, the two drugs can be administered simultaneously or one can be given before the other, i.e., a period of 30 minutes to one, two, or four hours can be allowed to lapse after the administration of the first drug before the second drug is administered.

Hypoxia Activated Drug Administration

In one aspect, the present invention provides a method of treating cancer comprising administering a therapeutically effective amount of a hypoxia activated prodrug of Formula I and a therapeutically effective amount of a Chk1 inhibitor to a patient in need of such treatment thereby treating the cancer. In one embodiment, the combination therapy is administered to a patient that has been previously treated with a Chk1 inhibitor or a hypoxia activated prodrug of Formula I, but the cancer is progressing despite the therapy, or the therapy has been discontinued due to cancer progression. In other embodiments, the patient has not been previously treated with any anti-cancer drug. In other embodiments, the patient has been previously treated with an anti-cancer drug other than a Chk1 inhibitor or a hypoxia activated prodrug of Formula I.

In one embodiment, the hypoxia activated prodrug of Formula I is selected from the group consisting of TH-281, TH-302, and TH-308. In one embodiment, the hypoxia activated prodrug administered is TH-302. In various embodiments, the TH-302 or other hypoxia activated prodrug of Formula I is administered once daily, once every 3 days, weekly, or once every 3 weeks. In one embodiment, the TH-302 or other hypoxia activated prodrug of Formula I is administered parenterally. In another embodiment, the TH-302 or other hypoxia activated prodrug is administered orally (see PCT application no. PCT/US2012/033671, filed Apr. 13, 2012, incorporated herein by reference).

In one embodiment, the hypoxia activated prodrug is TH-302, which is administered in a daily dose of about 240 m g/m² to about 670 mg/m². Suitable administration schedules for doses of TH-302 in this range include the following:

once a week at 575 mg/m²;
once every three weeks at 670 mg/m²;
days one and eight of a twenty-one day cycle at 300, 340, or 480 mg/m²;
days one, eight, and fifteen of a twenty-one day cycle at 240 or 340 mg/m²;
days one, four, eight, and eleven of a twenty-one day cycle at 240 to 480 mg/m²;
days one to five of a twenty-one day cycle at 460 mg/m²;
days one, eight, and fifteen of a twenty-eight day cycle at 240 to 575 mg/m²;
days eight, fifteen, and twenty-two of a twenty-eight day cycle at 240 to 575 mg/m², e.g. 480 mg/m², where the Chk1 inhibitor administration is initiated on day one; and
once every two weeks at 240 to 670 mg/m², which may follow surgery.

Each of the above schedules can be considered a "cycle" of therapy. Patients will generally receive more than one cycle of therapy, although there may be breaks of at least a day, and more generally a week or longer, between each cycle of therapy. Other compound of Formula I are generally dosed in accordance with the above schedules and amounts, with the amount adjusted to reflect how active the compound is relative to TH-302.

When a Chk1 inhibitor is combined with a hypoxia activated prodrug according to the present invention, the Chk1 inhibitor is contemplated to be administered in amounts and dosing frequencies as disclosed herein below, or in amounts and frequencies apparent to the skilled artisan in view of this disclosure, or in amounts and frequencies approved by the FDA or other regulatory authority for use in the treatment of cancer.

In various embodiments, the patient's cancer treated is a metastatic cancer or a refractory and/or relapsed cancer that is refractory to first, second, or third line treatment. In another embodiment, the treatment is a first, a second, or a third line treatment. As used herein, the phrase "first line" or "second line" or "third line" refers to the order of treatment received by a patient. First line treatment regimens are treatments given first, whereas second or third line treatment are given after the first line therapy or after the second line treatment, respectively. Therefore, first line treatment is the first treatment for a disease or condition. In patients with cancer, primary treatment can be surgery, chemotherapy, radiation therapy, or a combination of these therapies. First line treatment is also referred to those skilled in the art as primary therapy or primary treatment. Typically, a patient is given a subsequent chemotherapy regimen because the patient did not show a positive clinical or only showed a sub-clinical response to the first line therapy, or the first line treatment has stopped. In this context, "chemotherapy" is used in its broadest sense to incorporate not only classic cytotoxic chemotherapy but also molecularly targeted therapies and immunotherapies.

In another aspect, the treatment methods of the present invention are used for treating hyperproliferative diseases other than cancer.

Methods of preparation of and pharmaceutical compositions of hypoxia activated prodrugs, and other methods of treating cancer by administering various hypoxia activated prodrugs of Formula I are described in Duan et al., *J. Med. Chem.* 2008, 51, 2412-2420, and PCT Pub. Nos. 2007/002931, 2008/083101, and 2010/048330, each of which is incorporated herein by reference.

Other methods of treating cancers, which may be used in combination with the methods of the present invention, are known to one of skilled in the art, and are described, for example, in the product descriptions found in the 2010 or more current edition of the Physician's Desk Reference, Medical Economics Company, Inc., Oradell, N.J.; Goodman and Gilman's The pharmacological basis of therapeutics, Eds. Hardman et al., McGraw-Hill. New York. (US) 2011, 12th Ed., and in publications of the U.S. Food and Drug Administration and the NCCN Guidelines (National Comprehensive Cancer Network). Such methods can be appropriately modified by one of skill in the art, in view of this disclosure, to practice the treatment methods of the present invention.

In one embodiment, the TH-302 is provided in 100 mg vials, lyophilized, and dissolved in D5W and administered intravenously (i.v.) over approximately 30-60 minutes via an infusion pump. The infusion volume depends on the total dose given (in mg) during the infusion. If less than about 1000 mg is being infused, about 500 mL of D5W are used for infusion. If the total dose is greater than about 1000 mg, about 1000 mL of D5W are used for infusion.

Chk1 Inhibitors and their Administration

The following compounds are useful for administration in combination with a hypoxia activated prodrug of Formula I according to the present invention.

AZD7762 (see FIG. 1) is a Chk1 inhibitor with an $IC_{50}$ of 5 and <10 nM for Chk1 and Chk2, respectively. For treating cancer, AZD7762 has previously been administered (6, 9, 14, 21, 32, 48, 64, 96, and 144 mg) by i.v. infusion in combination with irinotecan (100 or 125 mg/m² i.v.), and by i.v. infusion (6, 9, 14, 21, 32, 40 mg) in combination with gemcitabine (for example, at 750 mg/m² and 1000 mg/m²), as described below (see, Sausville et al., J. Clin. Oncol., 29: 2011 (suppl; abstr 3058), incorporated herein by reference). Thus, AZD7762 was administered alone on days 1 and 8 (Cycle 0), and after 7 days' observation, AZD7762 was administered after irinotecan on days 1 and 8 of 21-day cycles. When combined with irinotecan, the dose limiting toxicity of AZD7762 was 96 mg with irinotecan at 100 mg/m². At 96 mg, AZD7762 showed cardiac side effects. When combined with gemcitabine, the dose limiting toxicity of AZD7762 was 30 mg.

Accordingly, in one embodiment of the present invention, AZD7762 is administered in a daily amount of up to but not exceeding 144 mg. In other embodiments, the daily amount of AZD7762 administered is up to but not exceeding 96 mg, 64 mg, 48 mg, 32 mg, and 30 mg. Thus, in various embodiments, AZD7762 is administered in a daily amount of 6, 9, 14, 21, 32, 40, 48, 64, 96, or 144 mg. In various embodiments, AZD7762 is administered once weekly. In various embodiments, AZD7762 is administered once weekly for 2 weeks followed by a week's AZD7762 holiday. In some embodiments, AZD7762 is co-administered with irinotecan or gemcitabine in combination with a hypoxia activated prodrug of Formula I, e.g. TH-302), and the irinotecan or gemcitabine is administered at doses and frequencies described above.

LY2603618 (IC-83; see FIG. 1) is a selective Chk1 inhibitor. For treating solid advanced or metastatic tumors, LY2603618 (at a dose of 170 mg or 230 mg) has been administered by i.v. infusion on days 2, 9 and 16 of at least one 28-day cycle in combination with gemcitabine (dosed at 1000 mg/m²) administered intravenously on days 1, 8 and 15 of at least one 28-day cycle. For treating pancreatic cancer, LY2603618 has been administered (at a dose of 70-300 mg/m², by i.v. infusion) once weekly for 3 weeks followed by 1 week of no treatment, repeated every 28 days for a minimum of 2 cycles in combination with gemcitabine administered 1000 mg/m², i.v., once weekly for 3 weeks followed by 1 week of no treatment, repeated every 28 days for a minimum of 2 cycles. LY2603618 has also been administered to cancer patients at a dose of 40 mg/m², with a possibility of dose escalation, on days 1 and 9 of cycle 1, and day 2 of subsequent cycles of unlimited 21 day cycles in combination with pemetrexed (500 mg/m², i.v.) administered on day 8 of cycle 1 and on day 1 of subsequent cycles of unlimited 21 day cycles. LY2603618 has also been administered to cancer patients, after prior treatment with a 50 mg oral dose of desipramine administration on day 1 of cycle 1, at a dose of 275 mg delivered by intravenous infusion followed by a 50 mg oral dose of desipramine on day 1 of cycle 2. In these studies, additional doses of LY2603618 in combination with other agents were contemplated as follows: 1000 mg/m² intravenous dose of gemcitabine on days 1, 8, and 15 and 230 mg intravenous doses of LY2603618 on days 2, 9 and 16 of 28 day cycles; and 500 mg/m² intravenous dose of pemetrexed on day 1 and 275 mg intravenous dose of LY2603618 on day 2 of 21 day cycles. In accordance with the methods of the invention, a hypoxia activated prodrug of Formula I, e.g. TH-302, can be administered in combination with LY2603618 administered at any of the foregoing doses and dosing frequencies and with or without co-administration of desipramine, pemetrexed, and gemcitabine.

Accordingly, in one embodiment of the present invention, LY2603618 is administered in a daily amount of 40-300 mg/m² (about 70-510 mg) in combination with a hypoxia activated prodrug of Formula I. In various embodiments, LY2603618 is administered in a daily amount of 70, 170, 230, or 275 mg. In various embodiments, LY2603618 is administered in a daily amount of 70-300 mg/m² or about 120-510 mg. In various embodiments, LY2603618 is administered once weekly. In various embodiments, LY2603618 is administered for 3 weeks followed by a week of no administration of LY2603618. In other embodiments, LY2603618 is administered once every three weeks.

CHIR-124, which inhibits Chk1 with an $IC_{50}$ of 0.3 nM, is another Chk1 inhibitor useful in accordance with the methods of the present invention.

SCH 900776 inhibits Chk1, cyclin dependent kinase 2 (CDK2), and Chk2 with $IC_{50}$ values of 3 nM, 0.16 µM, and 1.5 µM, respectively, and so is another Chk1 inhibitor useful in accordance with the methods of the present invention. For treating advanced solid tumors, SCH 900776 has been administered at 10, 20, 40, 80, and 112 mg/m$^2$ alone and following gemcitabine (800 mg/m$^2$) administration on days 1 and 8 every 21 days.

Accordingly, in one embodiment of the present invention, SCH 900776 is administered in a daily amount of up to 112 mg/m$^2$ (e.g. up to 190 mg) in combination with a hypoxia activated prodrug of Formula I, e.g. TH-302. In some embodiments, gemcitabine is also co-administered. In various embodiments, the daily amount of SCH 900776 administered is 10, 20, 40, 80, or 112 mg/m$^2$ (e.g. 17, 34, 68, 136, or 190 mg). In various embodiments, SCH 900776 is administered once weekly. In various embodiments, SCH 900776 is administered in a 3 week cycle, once weekly for two weeks, followed by a week of no treatment with SCH 900776.

PF-00477736 (PF477736) is a Chk1 inhibitor useful in accordance with the methods of the present invention. In some embodiments, Chk1 and a compound of Formula I, e.g., TH-302, are co-administered to treat cancer, and in other embodiments, additional anti-cancer agents are used. For example, PF-00477736 can be used for treating advanced solid tumors when administered in combination with a compound of Formula I, e.g., TH-302, and gemcitabine. In any of these embodiments escalating doses of PF-00477736 or any dose in the range of 750 to 1250 mg/m$^2$ can be administered intravenously on days 2 and 9 and gemcitabine administered intravenously on days 1 and 8 of a 21-day cycle, in combination with a compound of Formula I, e.g., TH-302, administered as described herein. If a patient is administered a dose at Cycle 0, then, in some embodiments, PF-0047736 is administered intravenously on days 1 and 8 of a 21-day cycle for patients who have a 3-hour infusion, and on days 1 and 8 of a 14-day cycle for patients who have a 24-hour infusion, and gemcitabine is administered intravenously on days 1 and 8 of a 21-day cycle.

Accordingly, in one embodiment of the present invention, PF-00477736 is administered in a daily amount of up to 1250 mg/m$^2$ (e.g. up to 2125 mg) in combination with a hypoxia activated prodrug of Formula I, e.g. TH-302. In some embodiments, gemcitabine is also co-administered. In various embodiments, the daily amount of PF-00477736 administered is 750, 800, 850, 900, 950, 1000, 1050, 1100, 1150, 1200, or 1250 mg/m$^2$ (e.g. from 1275 to 2125 mg in increments of 85 mg). In various embodiments, PF-00477736 is administered once weekly. In various embodiments, PF-00477736 is administered in a 3 week cycle, once weekly for two weeks, followed by a week of no treatment with PF-00477736, or is administered in a 2 week cycle, once weekly for two weeks. PF-0477736 can also be used for treating Philadelphia-positive acute lymphoblastic leukemia (Ph+ ALL), diffuse large B-cell lymphoma, and such other types of blood cancers in combination with hypoxia activated prodrugs of Formula I.

Thus, in accordance with the present invention, TH-302 or another compound of Formula I is co-administered with a Chk1 inhibitor, optionally in combination with other treatments. A synergistic effect may be achieved by using more than one compound in a pharmaceutical composition of the invention, i.e. a compound of Formula I is combined with at least another agent as active ingredient, which is either another compound of Formula I, or a Chk1 inhibitor, or both, or another anti-cancer agent. The active ingredients useful in the methods of the invention can be used either simultaneously (as in an admixed formulation) or sequentially. Thus, the invention also relates to a compound or pharmaceutical composition for inhibiting abnormal cell growth or cancer in a mammal which comprises an amount of a compound of Formula I, or a pharmaceutically acceptable salt or solvate or prodrug thereof, in combination with an amount of another Chk1 inhibitor (and optionally another anti-cancer therapeutic), wherein the amounts of the compound, salt, solvate, or prodrug, and of the Chk1 inhibitor (and of the another anti-cancer therapeutic) are together effective in inhibiting abnormal cell growth or cancer in a patient. The combination therapies described herein are thus suitable for use in combination with known anti-cancer agents.

The invention also relates to a set of items, which may be packaged into a kit, consisting of separate packs of an effective amount of a compound of Formula I and a Chk1 inhibitor (or pharmaceutically acceptable salts, derivatives, solvates, and stereoisomers thereof, including mixtures thereof in all ratios, and optionally an effective amount of a further medicament active ingredient). The set or kit comprises suitable containers, such as boxes, individual bottles, bags, or ampoules. The set may, for example, comprise separate ampoules, each containing an effective amount of a compound of Formula I and a Chk1 inhibitor (or pharmaceutically acceptable salts, derivatives, solvates, and stereoisomers thereof, including mixtures thereof in all ratios, and optionally an effective amount of a further medicament active ingredient), each in dissolved or lyophilized form. The set or kit of the invention may also contain an article that contains written instructions or directs the user to written instructions that explain the how the compounds are administered in accordance with the invention to treat a disease, such as cancer.

The invention also relates to the use of compounds of Formula I and Chk1 inhibitor compounds and/or physiologically acceptable salts thereof for the prophylactic or therapeutic treatment and/or monitoring of diseases, such as cancer, that are caused, mediated, and/or propagated by abnormal cellular proliferative activity.

Furthermore, the invention relates to the use of compounds of Formula I and Chk1 inhibitors and/or physiologically acceptable salts thereof for the production of a medicament for the prophylactic or therapeutic treatment and/or monitoring of diseases, such as cancer, that are caused, mediated, and/or propagated by abnormal cellular proliferative activity.

Compounds of Formula I and Chk1 inhibitors and/or a physiologically acceptable salt thereof can also be employed as intermediates for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of Formula I and Chk1 inhibitors according to the invention and/or physiologically acceptable salts thereof for use in the prophylactic or therapeutic treatment and/or monitoring of diseases, such as cacner, that are caused, mediated, and/or propagated by abnormal cellular proliferative activity. Another preferred object of the invention concerns compounds of Formula I and Chk1 inhibitors according to the invention and/or physiologically acceptable salts thereof for use in the prophylactic or therapeutic treatment and/or monitoring of hyperproliferative disorders, including cancer.

The prior teaching of the present specification concerning the compounds of Formula I and Chk1 inhibitors, including any preferred embodiment thereof, is valid and applicable without restrictions to the compounds Formula I and Chk1 inhibitors and their salts for use in the prophylactic or therapeutic treatment and/or monitoring of hyperproliferative disorders.

The following examples illustrate various aspects and embodiment of the invention.

EXAMPLES

Example 1

Enhanced TH-302 Activity in Both p53 Deficient Hela Cells and HT29 Cells by CHK1 Inhibitors Cells were treated with TH-302 and a Chk1 inhibitor (0.4 µM PF477736, 0.1 µM AZD7762, or 0.5 µM LY2603618) for 2 hours under under either normoxia or hypoxia. After a wash to remove drugs, cells were incubated with fresh media at 37° C. for an additional 3 days in the presence of a Chk1 inhibitor. Cell viability was determined using AlamarBlue. For a doxorubicin group (doxorubicin also induces cell cycle arrest in the G2/M phase and was used as a non-hypoxia activated prodrug control), cells were co-treated with doxorubicin and Chk1 inhibitors for 3 days. The results demonstrated that TH-302 activity in both Hela cells and HT29 cells was significantly enhanced by the presence of Chk1 inhibitors. A similar enhancement of doxorubicin activity was also observed in the presence of a Chk1 inhibitor. The $IC_{50}$ values in µM obtained are provided in FIG. 2.

Example 2

TH-302 Activity is not Altered by Chk1 Inhibitor in p53 Heterozygous DU145 and p53 Wild Type H460 Cells Appropriate Du145 and H460 cells were treated with TH-302 and Chk1 inhibitors as described in Example 1. The results demonstrated that TH-302 activity in both Du145 cells and H460 cells was not enhanced by the presence of Chk1 inhibitors. A similar lack of enhanced activity of doxorubicin activity was also observed in the presence of a Chk1 inhibitor. These results are consistent with the presence in these cells of a functional p53 pathway for mediating DNA repair. The $IC_{50}$ values in µM obtained are provided in FIG. 2.

Example 3

Enhanced TH-302 Activity by Chk1 Inhibitors in p53 Deficient Cells but not in p53 Proficient Cells Cells (provided by Horizon Discovery Ltd. and generated using Horizon's adeno-associated virus (AAV) technology Genesis™) were treated as described in Example 1. The results demonstrated that TH-302 activity was significantly enhanced by co-treatment with a Chk1 inhibitor in p53 deficient cells but not p53 proficient cells. Similar results were obtained for doxorubicin. The $IC_{50}$ values in µM obtained are provided in FIG. 2.

Example 4

Chk1 Inhibitor Abrogates TH-302-Mediated Cell-Cycle Arrest and Cdc2-Y15 Phosphorylation HeLa cells were treated with TH-302 and a Chk1 inhibitor as described in Example 1. Cells were harvested and analyzed for cell cycle distribution by flow cytometry and for protein expression by immunoblot. The results demonstrated that TH-302 exhibited concentration-dependent cell cycle arrest at $G_2/M$, and the $G_2/M$ arrest-mediated by TH-302 was abrogated by the Chk1 inhibitor, supporting Chk1 kinase's role in TH-302-mediated $G_2/M$ arrest. Immunoblot data demonstrated DNA-damaging agents TH-302 and doxorubicin upregulate phosphorylation of Cdc2-Y15, and the Chk1 inhibitor completely eliminated the DNA damaging agent-induced increase of Cdc2-Y15 phosphorylation. The Chk1 inhibitor alone did not affect Cdc2-Y15 phosphorylation.

Example 5

Enhancement of TH-302's Antitumor Activity by AZD7762 in HT29 Xenografts

Figure 4A:
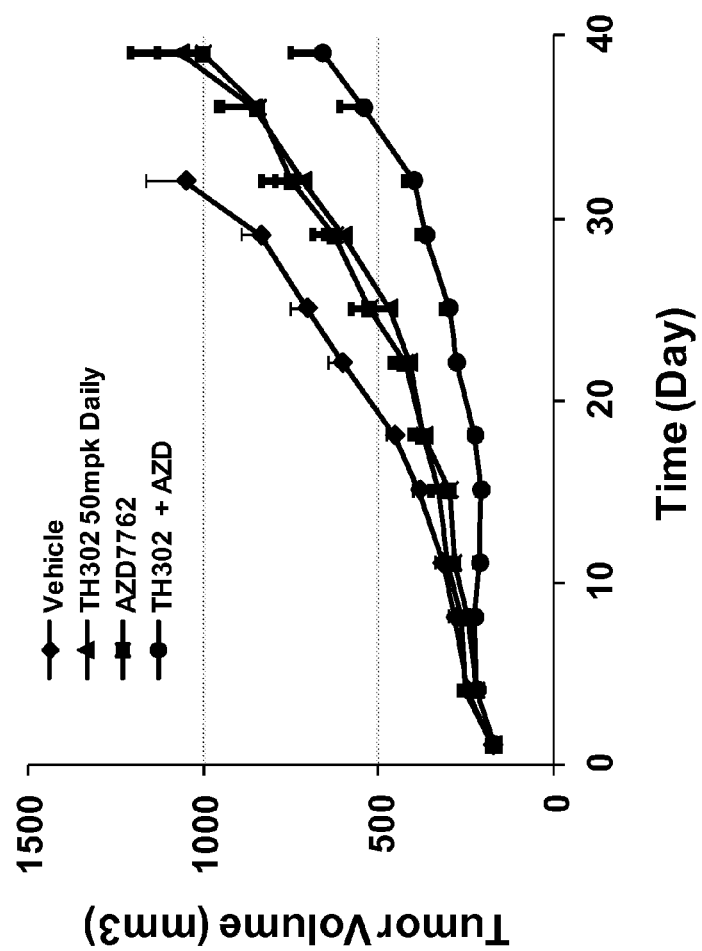
FIGS. 4A(I)-(III) show the results of daily dosing of TH-302 in the animal model study described in Example 5 below.
Figure 4B:
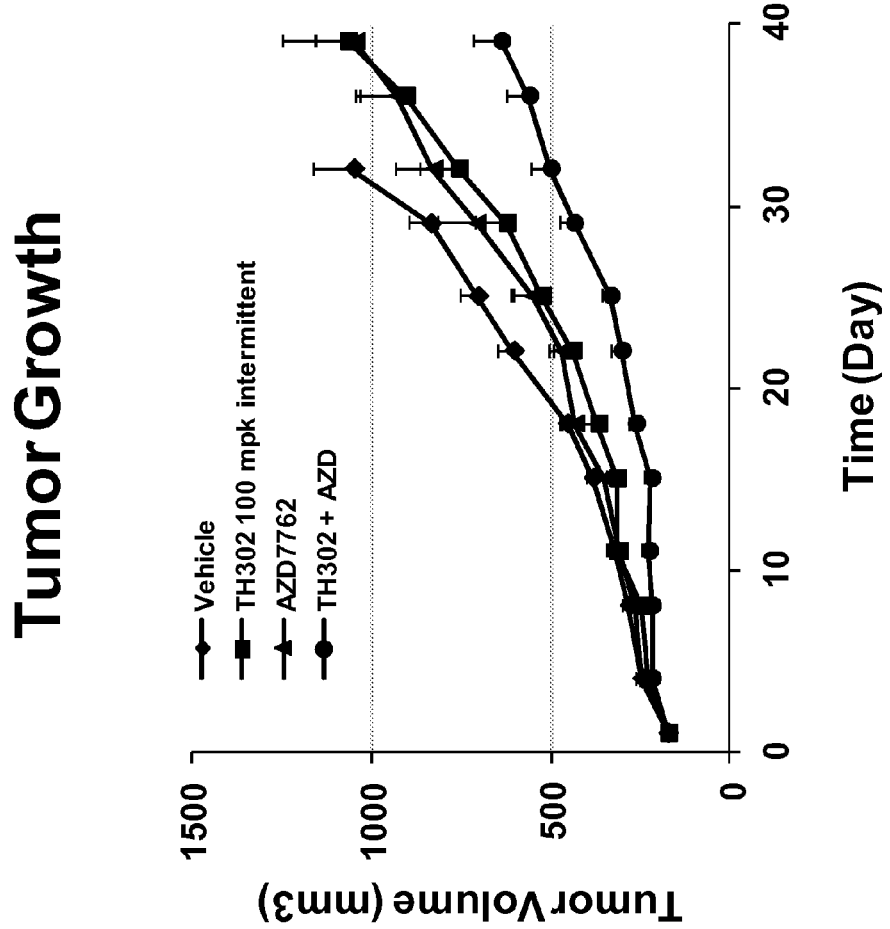
FIGS. 4B(I)-(III) show the results of intermittent dosing in the animal model study described in Example 5 below.

HT-29 tumor-bearing mice were treated with TH-302 alone, AZD7762 alone, and TH-302 in combination with AZD7762. TH-302 was dosed intraperitoneally (i.p.) at either 50 mg/kg, QD×5/wk×2 wks (daily dosing), or 100 mg/kg, twice/wk×2 wks (intermittent dosing). AZD7762 was dosed i.p. at either 12.5 mg/kg, QD×5/wk×2 wks, or 12.5 mg/kg, four times/wk×2 wks. For the combination therapy, two dose regimens were used: TH-302 at QD×5/wk×2 wks and AZD7762 at 12.5 mg/kg, QD×5/wk×2 wks, with AZD7762 dosed 4 hours after TH-302 administration; and TH-302 at 100 mg/kg, twice/wk×2 wks and AZD7762 at 12.5 mg/kg, four times/wk×2 wks, with AZD7762 dosed 4 hours and 16 hours after TH-302. The data (shown in FIGS. 4A-B) demonstrated that TH-302 alone or AZD7762 alone produced a growth delay, and that the combination of AZD7762 with TH-302 significantly prolonged the time required for tumor volume doubling relative to either drug alone.

These examples demonstrate that TH-302 activity is significantly enhanced by co-administration with a Chk1 inhibitor in p53 deficient tumor cell lines but not in p53 proficient cell lines; that Chk1 inhibitors can abrogate TH-302-mediated cell-cycle arrest; that TH-302 can increase phosphorylation of Cdc2-Y15 but does not affect the expression of Cdc-2, Myt1 and Chk1; that a Chk1 inhibitor can completely eliminate TH-302-induced increase of Cdc2-Y15 phosphorylation; and that co-administration of a Chk1 inhibitor significantly enhances TH-302-mediated anti-tumor activity in HT29 xenografts.

Example 6

Effect of Combination Therapy on DNA Damage in Cells

The preceding examples show that Chk1 inhibitors are TH-302 sensitizers both in vitro and in vivo in the context of p53 checkpoint deficiency. To assess the impact of the Chk1 inhibitor AZD7762 on DNA damage in TH-302 treated cells directly, the single-cell electrophoresis-based 'Comet' assay was employed. After seeding HT29 cells at $1 \times 10^6$ cells/3 ml/60 mm dish for 24 hr, TH-302 (at the indicated concentrations below) and 0.1 µM of AZD7622 were added and incubated for 24 hr either under air or 0.1% $O_2$. Cells were washed twice to remove the compounds. The Comet assay was performed with Trevigen's single-cell electrophoresis system (Gaithersburg, Md.). The olive tail moment was calculated using Comet Assay IV software from Perceptive Instruments (Suffolk, UK). The olive tail moment is the distance of DNA migration from the body of the nuclear core and provides an evaluation of the extent of DNA damage. HT29 cells treated (for 24 hr) with vehicle, TH-302 (10 µM with air; 2.5 µM with 0.1% $O_2$), or AZD7762 (0.1 µM with air) exhibited no visible tail moment (observed tail moment values of from 0.1 to 0.3). In contrast, cells treated with both AZD7762 and TH-302 exhibited an olive tail moment, indicating the induction of double-strand breaks: olive tail moments ranged from 3 (2.5 µM TH-302 and 0.1 µM AZD7762 in air) to 25 (10 µM TH-302 and 0.1 µM AZD7762 in 0.1% $O_2$).

To determine the effect of AZD7762 on TH-302-induced DNA damage response, γH2AX was evaluated. HT29 cells were treated with vehicle or TH-302 for 2 hr under either exemplary normoxic (95% air/5% $CO_2$, TH-302 at 0-50 µM) or exemplary hypoxic (90% $N_2$/5% $CO_2$/5% $H_2$; TH-302 at 0-5 µM) conditions with or without 0.1 µM of AZD7762. After washing, cells were continuously incubated for additional 4 hr in the presence of 0.1 µM AZD7762. HT29 cells were permeabilized with 1% Triton X-100 and incubated with γH2AX monoclonal antibody for 2 hr and goat anti-mouse-FITC for 1 hr. Cells were imaged using a fluorescent microscope (Nikon TS-100). The results showed that, in $p53^{-/-}$ HT29 cells, TH-302 alone and AZD7762 alone could induce γH2AX. However, treatment with both AZD7762 and TH-302 greatly increased γH2AX staining, demonstrating a greater DNA damage response with the combination therapy.

Induction of apoptosis was also assessed. HT29 cells were seeded at a density of 40,000 cells per well of a 24 well plate. After 24 hr incubation for cell attachment, cells were exposed to TH-302 (0-10 µM under air and 0-1 µM under $N_2$) and 0.1 µM of AZD7762 for 2 hr. After washing, cells were continuously cultured for an additional 46 hr in the presence of 0.1 µM of AZD7762. A luminescence-based caspase activity assay was performed. TH-302 did not induce apoptosis in HT29, while AZD7762 caused a slight increase in apoptosis (Caspase Glo3/7 Assay System, Promega). However, treatment with both TH-302 and AZD7762 induced a 3-fold increase in apoptosis, indicating that the Chk1 inhibitor AZD7762 sensitizes HT29 cells, for example, to apoptosis in response to the DNA damage induced by TH-302. To validate the specificity of apoptotic signal, the pan-caspase inhibitor ZVAD was included in the testing. ZVAD reduced the apoptotic signal generated by the combination therapy, consistent with the apoptosis induced being a caspase-dependent process.

To explore involved signaling pathways, an immunoblot analysis was conducted. HT29 cells were seeded in p60 dishes at a density of $2 \times 10^6$ cells per dish and incubated overnight for cell attachment. The following day, cells were exposed to TH-302 (50 µM in air and 1 µM in $N_2$), 0.1 µM AZD7762 or the combination of TH-302 and AZD7762 for 2 hr under either normoxia (air) or anoxia ($N_2$). After TH-302 was removed by washing, cells were continuously incubated with AZD7762 for 22 hours and then lysed with a protease inhibitor cocktail and brief sonication. Insoluble debris was pelleted and the protein concentration of the resulting supernatant determined using a Sigma BCA kit (St. Louis, Mo.). About 10 µg of protein from each sample were loaded onto and SDS gel and electrophoresed and then electrotransferred to a nitrocellulose membrane. Proteins were detected with an electrochemiluminescent detection system (ChemiGlow; Protein Simple, Santa Clara, Calif.) using antibodies recognizing Histone H3. An increase in phospho-histone H3 (at serine 10) was observed in the combination treatment group but not in the TH-302 treated or AZD7762-treated samples, consistent with DNA damaged cells undergoing mitotic catastrophe (TH-302 causes a G2 cell cycle arrest, and AZD7762 unblocks the G2 arrest). Equal loading was confirmed by actin blot, which showed even intensities across the samples.

To investigate which DNA repair system is affected by Chk-1 inhibitor-mediated enhancement of TH-302 cytotoxicity, CHO cell-based DNA repair mutant cell line pairs were utilized. The experimental details were as described in Example 1. The data showed that potentiation of TH-302 cytotoxicity by AZD7762 (0.1 µM) was observed only in cell lines proficient in HDR (AA8 CHO cells; TH-302 $IC_{50}$ was 260 µM in air and 1.2 µM in $N_2$) and not cell lines deficient in HDR (cell lines irsl SF and UV41: TH-302 $IC_{50}$ was 63 µM (irs1SF) and 26 µM (UV41) in air and 0.3 µM (irs1SF) and 0.06 µM (UV41) in $N_2$). HDR (homology-dependent repair) is the specific type of DNA repair capable of repairing TH-302-induced DNA damage. The $IC_{50}$ of TH-302 monotherapy in AA8, irs1SF, and UV41 cell lines in air is 490 µM, 54 µM, and 29 µM, respectively, and in $N_2$ is 3.2 µM, 0.4 µM, and 0.07 µM, respectively.

To explore the role of HDR in AZD7762-mediated potentiation of TH-302 cytotoxicity further, the effects of AZD7762 on Rad51, an enzyme that coordinates recombination and that is important to the process of error-free DNA repair by recombination, levels were examined. The samples were collected as described above for the Histone H3 blot. In response to TH-302, Rad51 expression levels were increased. However, the combination treatment with AZD7762 and TH-302 led to Rad51 expression levels lower than those observed in control cells. The results are consistent with down-regulation of Rad51-dependent HDR by AZD7762 resulting in the persistence of unrepaired DNA damage caused by TH-302, providing a mechanism for potentiation of TH-302 cytotoxicity by AZD7762.

The data presented in this example support a new approach for the treatment of cancer in which a Chk1 inhibitor is administered in combination with a tumor-hypoxia targeted prodrug such as TH-302 or another compound of Formula I to provide more efficacious therapy.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The invention has been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

The invention claimed is:

1. A method of treating cancer, said method comprising administering to a patient in need of such treatment a therapeutically effective amount of a hypoxia activated prodrug in combination with a therapeutically effective amount of a Chk1 inhibitor, wherein said patient is identified as having a p53-deficient cancer prior to administration of the hypoxia activated prodrug and the Chk1 inhibitor.

2. The method of claim 1, wherein the hypoxia activated prodrug is a compound of Formula I:

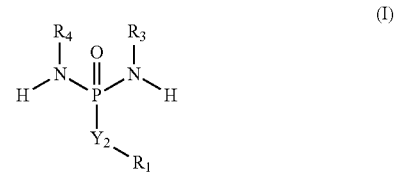

wherein
$Y_2$ is O, S, $NR_6$, $NCOR_6$, or $NSO_2R_6$
$R_6$ is $C_1$-$C_6$ alkyl, $C_1$-$C_6$ heteroalkyl, aryl, or heteroaryl;

$R_3$ and $R_4$ are independently selected from the group consisting of 2-haloalkyl, 2-alkylsulfonyloxyalkyl, 2-arylsulfonyloxyalkyl, and 2-heteroalkylsulfonyloxyalkyl;

$R_1$ has the formula $L-Z_3$;

L is $C(Z_1)_2$;

each $Z_1$ independently is hydrogen, halogen, $C_1$-$C_6$ alkyl, $C_1$-$C_6$ heteroalkyl, aryl, heteroaryl, $C_3$-$C_8$ cycloalkyl, heterocyclyl, $C_1$-$C_6$ acyl, $C_1$-$C_6$ heteroacyl, aroyl, or heteroaroyl;

or L is:

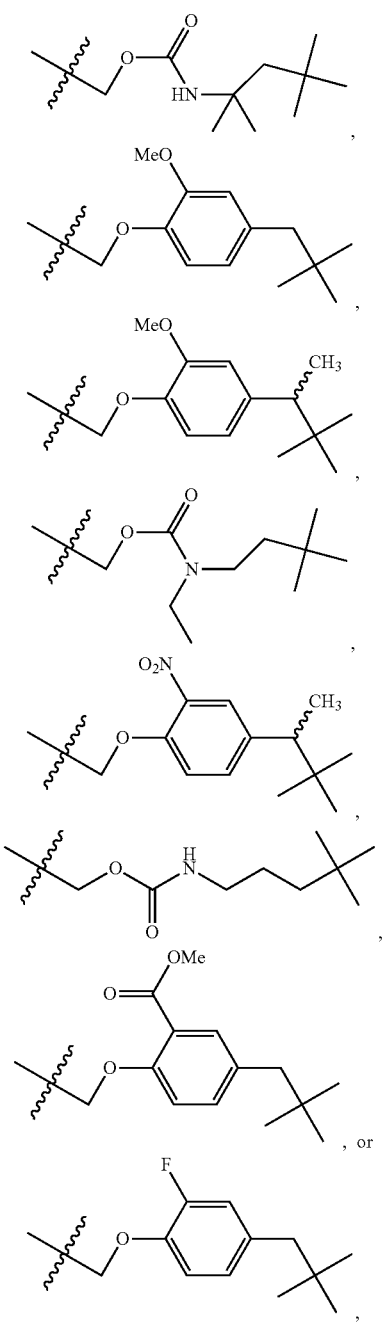

$Z_3$ is a bioreductive group having a formula selected from the group consisting of:

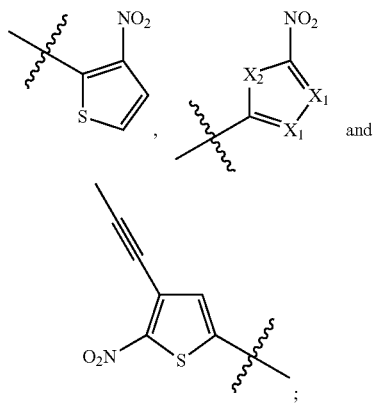

each $X_1$ is independently N or $CR_8$;

$X_2$ is $NR_S$, S, or O;

each $R_7$ is independently $C_1$-$C_6$ alkyl, $C_1$-$C_6$ heteroalkyl, $C_3$-$C_8$ cycloalkyl, heterocyclyl, aryl or heteroaryl;

and $R_8$ is independently hydrogen, halogen, cyano, $CHF_2$, $CF_3$, $CO_2H$, amino, $C_1$-$C_6$ alkyl, $C_1$-$C_6$ heteroalkyl, $C_1$-$C_6$ cycloalkyl, $C_1$-$C_6$ alkoxy, $C_1$-$C_6$ alkylamino, $C_1$-$C_6$ dialkylamino, aryl, $CON(R_7)_2$, $C_1$-$C_6$ acyl, $C_1$-$C_6$ heteroacyl, aroyl or heteroaroyl;

or a pharmaceutically acceptable salt thereof.

3. The method of claim 2, wherein said compound of Formula I is TH-302.

4. The method of claim 2, wherein said Chk1 inhibitor is selected from the group consisting of AZD7762, LY2603618, PF-00477736, and SCH 900776.

5. A pharmaceutical formulation comprising a compound of Formula I:

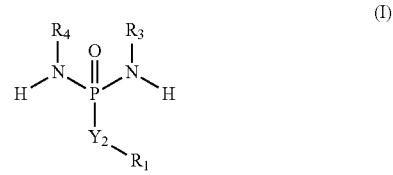

(I)

wherein $Y_2$ is O, S, $NR_6$, $NCOR_6$, or $NSO_2R_6$ $R_6$ is $C_1$-$C_6$ alkyl, $C_1$-$C_6$ heteroalkyl, aryl, or heteroaryl;

$R_3$ and $R_4$ are independently selected from the group consisting of 2-haloalkyl, 2-alkylsulfonyloxyalkyl, 2-arylsulfonyloxyalkyl, and 2-heteroalkylsulfonyloxyalkyl;

$R_1$ has the formula $L-Z_3$;

L is $C(Z_1)_2$;

each $Z_1$ independently is hydrogen, halogen, $C_1$-$C_6$ alkyl, $C_1$-$C_6$ heteroalkyl, aryl, heteroaryl, $C_3$-$C_8$ cycloalkyl, heterocyclyl, $C_1$-$C_6$ acyl, $C_1$-$C_6$ heteroacyl, aroyl, or heteroaroyl;

or L is:

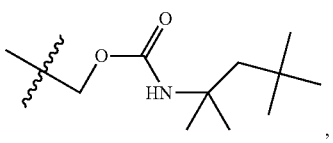

-continued

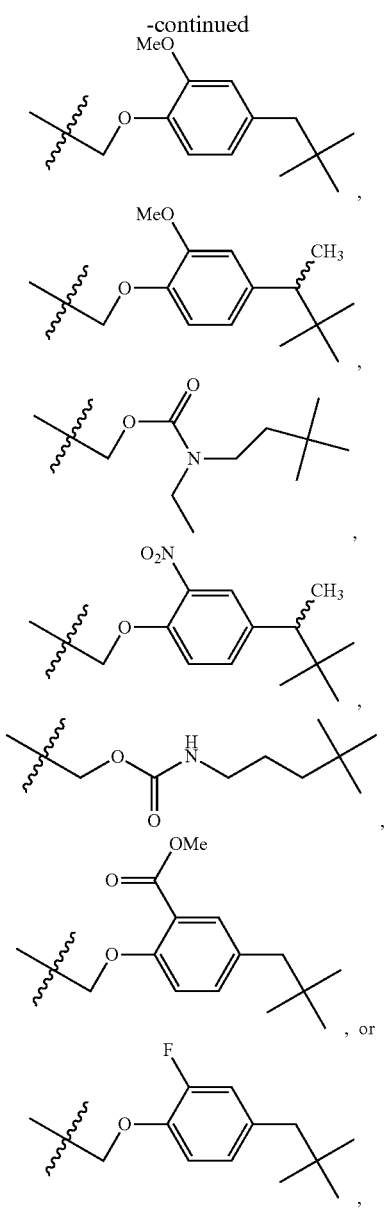

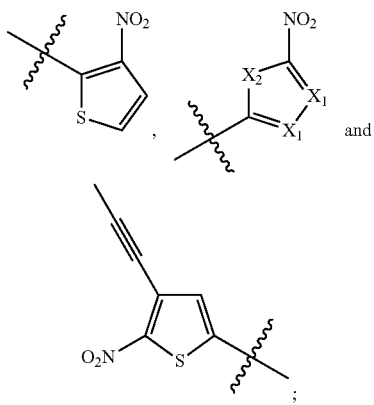

each $X_1$ is independently N or $CR_8$;
$X_2$ is $NR_S$, S, or O;

each $R_7$ is independently $C_1$-$C_6$ alkyl, $C_1$-$C_6$ heteroalkyl, $C_3$-$C_8$ cycloalkyl, heterocyclyl, aryl or heteroaryl;

and $R_8$ is independently hydrogen, halogen, cyano, $CHF_2$, $CF_3$, $CO_2H$, amino, $C_1$-$C_6$ alkyl, $C_1$-$C_6$ heteroalkyl, $C_1$-$C_6$ cycloalkyl, $C_1$-$C_6$ alkoxy, $C_1$-$C_6$ alkylamino, $C_1$-$C_6$ dialkylamino, aryl, $CON(R_7)_2$, $C_1$-$C_6$ acyl, $C_1$-$C_6$ heteroacyl, aroyl or heteroaroyl;

or a pharmaceutically acceptable salt thereof;

a Chk1 inhibitor, and at least a pharmaceutically acceptable excipient.

6. The pharmaceutical formulation of claim 5, wherein said compound of Formula I is TH-302.

7. The pharmaceutical formulation of claim 6 wherein said Chk1 inhibitor is selected from the group consisting of AZD7762, LY2603618, PF-00477736, and SCH 900776.

8. A method of increasing antitumor effect of a compound of Formula I:

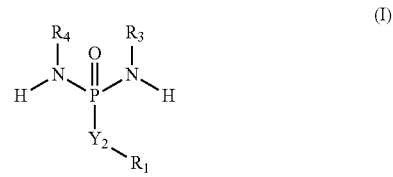

wherein $Y_2$ is O, S, $NR_6$, $NCOR_6$, or $NSO_2R_6$ $R_6$ is $C_1$-$C_6$ alkyl, $C_1$-$C_6$ heteroalkyl, aryl, or heteroaryl;

$R_3$ and $R_4$ are independently selected from the group consisting of 2-haloalkyl, 2-alkylsulfonyloxyalkyl, 2-arylsulfonyloxyalkyl, and 2-heteroalkylsulfonyloxyalkyl;

$R_1$ has the formula L-$Z_3$;

L is $C(Z_1)_2$;

each $Z_1$ independently is hydrogen, halogen, $C_1$-$C_6$ alkyl, $C_1$-$C_6$ heteroalkyl, aryl, heteroaryl, $C_3$-$C_8$ cycloalkyl, heterocyclyl, $C_1$-$C_6$ acyl, $C_1$-$C_6$ heteroacyl, aroyl, or heteroaroyl;

or L is:

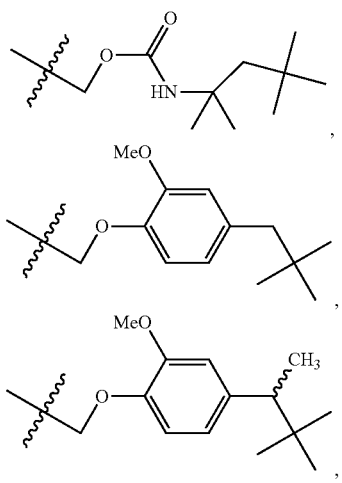

-continued

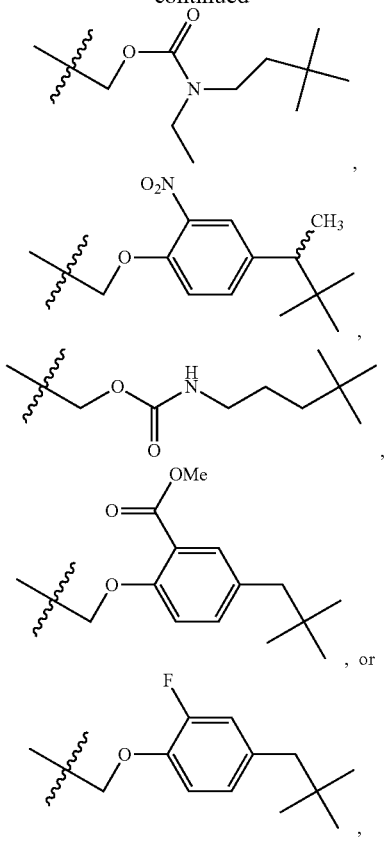

$Z_3$ is a bioreductive group having a formula selected from the group consisting of:

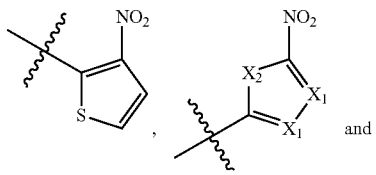

-continued

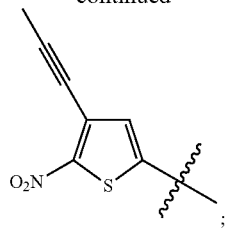

each $X_1$ is independently N or $CR_8$;

$X_2$ is $NR_S$, S, or O;

each $R_7$ is independently $C_1$-$C_6$ alkyl, $C_1$-$C_6$ heteroalkyl, $C_3$-$C_8$ cycloalkyl, heterocyclyl, aryl or heteroaryl;

and $R_8$ is independently hydrogen, halogen, cyano, $CHF_2$, $CF_3$, $CO_2H$, amino, $C_1$-$C_6$ alkyl, $C_1$-$C_6$ heteroalkyl, $C_1$-$C_6$ cycloalkyl, $C_1$-$C_6$ alkoxy, $C_1$-$C_6$ alkylamino, $C_1$-$C_6$ dialkylamino, aryl, $CON(R_7)_2$, $C_1$-$C_6$ acyl, $C_1$-$C_6$ heteroacyl, aroyl or heteroaroyl;

or a pharmaceutically acceptable salt thereof on a P53 deficient tumor cell, comprising coadministering to the tumor cell a Chk1 inhibitor.

9. The method of claim 8, wherein the Chk1 inhibitor is AZD7762, PF00477736, or LY603618.

10. The method of claim 8, wherein the compound of Formula I is TH-302.

11. The method of claim 3, wherein said Chk1 inhibitor is selected from the group consisting of AZD7762, LY2603618, PF-00477736, and SCH 900776.

12. The method of claim 9, wherein the compound of Formula I is TH-302.

13. A method of treating cancer, said method comprising administering to a patient in need of such treatment a therapeutically effective amount of a hypoxia activated prodrug in combination with a therapeutically effective amount of a Chk1 inhibitor, wherein said cancer is selected from bladder cancer, colon cancer, head and neck cancer, lung cancer, and ovarian cancer.

* * * * *